(12) United States Patent
McCaddon

(10) Patent No.: US 7,709,460 B2
(45) Date of Patent: May 4, 2010

(54) METHOD FOR TREATING OR PREVENTING A FUNCTIONAL VITAMIN B12 DEFICIENCY IN AN INDIVIDUAL AND MEDICAL COMPOSITIONS FOR USE IN SAID METHOD

(75) Inventor: Andrew McCaddon, Wrexham (GB)

(73) Assignee: Cobalz Limited, Chester, Cheshire (GB)

( * ) Notice: Subject to any disclaimer, the term of this patent is extended or adjusted under 35 U.S.C. 154(b) by 865 days.

(21) Appl. No.: 10/475,898

(22) PCT Filed: Apr. 22, 2002

(86) PCT No.: PCT/GB02/01843

§ 371 (c)(1),
(2), (4) Date: Apr. 12, 2004

(87) PCT Pub. No.: WO02/087593

PCT Pub. Date: Nov. 7, 2002

(65) Prior Publication Data

US 2004/0157783 A1 Aug. 12, 2004

(30) Foreign Application Priority Data

Apr. 25, 2001 (GB) ................. 0110336.5
Aug. 22, 2001 (GB) ................. 0120363.7

(51) Int. Cl.
*A01N 43/04* (2006.01)
*A01N 37/12* (2006.01)
*A01N 37/44* (2006.01)
*A61K 31/70* (2006.01)
*A61K 31/195* (2006.01)

(52) U.S. Cl. ........................ 514/52; 514/562
(58) Field of Classification Search ....................... None
See application file for complete search history.

(56) References Cited

U.S. PATENT DOCUMENTS

| 945,772 | A | * | 1/1910 | Evans | 15/152 |
| 4,940,658 | A | * | 7/1990 | Allen et al. | 435/4 |
| 5,668,117 | A | * | 9/1997 | Shapiro | 514/55 |
| 5,807,832 | A | * | 9/1998 | Russell-Jones et al. | 514/21 |
| 6,008,190 | A | * | 12/1999 | Meade et al. | 514/6 |
| 6,013,632 | A | * | 1/2000 | Jones et al. | 514/17 |
| 6,127,370 | A | | 10/2000 | Smith et al. | 514/250 |
| 6,207,190 | B1 | * | 3/2001 | Richardson et al. | 424/472 |
| 6,562,869 | B1 | * | 5/2003 | Hamilton et al. | 514/557 |
| 6,649,193 | B1 | * | 11/2003 | Colic | 424/600 |
| 6,787,527 | B1 | * | 9/2004 | Weinberg et al. | 514/52 |
| 6,812,248 | B2 | * | 11/2004 | Zhang et al. | 514/514 |

FOREIGN PATENT DOCUMENTS

| EP | 0 891719 | 1/1999 |
| GB | 945772 | 4/1960 |
| WO | WO / 9811900 | 3/1998 |
| WO | WO / 0043013 | 7/2000 |
| WO | WO / 0056295 | 9/2000 |
| WO | WO / 0126642 | 4/2001 |
| WO | WO / 0193865 | 12/2001 |

OTHER PUBLICATIONS

The Compact Oxford English Dictionary, AskOxford.com, electronic copy, p. 1.*
Brash et al. Synthesis and characterization of isolable thiolactocobalamin complexes relvant to coenzyme B12-dependent ribonuceloside triphosphate reductase. Journal of Inorganic Biochemistry. 1999;76:197-209; see abstract and pp. 204-205.*
Price. AIDS dementia Complex. HIV InSite Knowledge Base Cahpter. 1998; electronic pp. 1-11.*
De Rosa et al. N-acetylcysteine replenishes glutathione in HIV infection. European Journal of Clinical Investigation. 2000; 30: 915-929.*
Simpson et al. Human immunodeficiency virus-associated dementia: review of pathogenesis, prophylaxis, and treatment studies of zidovudine therapy. Clinical Infectious Diseases. 1999;29:19-34.*
American Psychiatric Association, *Diagnostic and Statistical Manual of Mental Disorders*, 4th ed., Washington, DC, APA, pp. 133-163 (1994).
Behl, C., "Alzheimer's Disease and Oxidative Stress: Implications for Novel Therapeutic Approaches," Prog. Neurobiol., vol. 57, pp. 301-323 (1999).
Bell, I.R. et al., "Plasma Homocysteine in Vascular Disease and in Nonvascular Dementia of Depressed Elderly People," Acta Psychiatr. Scand., vol. 86, No. 5, pp. 386-390 (1992).
Berr et al., "Cognitive Decline Associated with Systemic Oxidative Stress: The EVA Study," JAGS, vol. 48, pp. 1285-1291 (2000).
Budge, M. et al., "Plasma Total Homocysteine and Cognitive Performance in a Volunteer Population," Ann. N.Y. Acad. Sci., pp. 407-410 (1999).
Burns, A. et al., "Dietary Intake and Clinical Anthropometric and Biochemical Indices of Malnutrition in Elderly Demented Patients and Non-Demented Subjects," Psychol. Med., vol, 19, No. 2, pp. 383-391 (1989).
Carmel, R. et al., "Neurologic Abnormalities in Cobalamin Deficiency are Associated with Higher Cobalamin 'Analogue' Values Than are Haematological Abnormalities," J. Lab. Clin. Med., vol. 111, No. 1, pp. 57-62 (1988).

(Continued)

*Primary Examiner*—David J Blanchard
*Assistant Examiner*—Barbara Frazier
(74) *Attorney, Agent, or Firm*—Bonnie J. Davies; John H. Runnels

(57) ABSTRACT

A method and medical composition for the treatment and/or prevention of a functional Vitamin $B_{12}$ deficiency in an individual that is brought about as a consequence of oxidative stress on biochemical pathways. The functional Vitamin $B_{12}$ deficiency may eventually present as dementia, other neuropsychiatric abnormality and/or vascular disease. The method involves the administration of a medical composition that supplies a cobalt-sulphur bond in the upper β-ligand of an intracellular cobalamin molecule thereby facilitating intracellular processing of cobalamin. The cobalt-sulphur bond may be provided directly by administration of a thiolatocobalamin, such as glutathionyl-cobalamin or indirectly by the co-administration of Vitamin $B_{12}$ (or a derivative thereof) with a sulphur-containing molecule, such as glutathione or a precursor thereof.

10 Claims, 4 Drawing Sheets

OTHER PUBLICATIONS

Cecchi, C. et al., "Gluthathione (stet) Level is Altered in Lymphoblasts from Patients with Familial Alzheimer's Disease," Neuroscience Letters, vol. 275, pp. 152-154 (1999).

Chen et al., "Homocysteine Metabolism in Cardiovascular Cells and Tissues: Implications for Hyperhomocysteinemia and Cardiovascular Disease," Adv. Enzyme Regul., vol. 39, pp. 93-109 (1999).

Christen, Y., "Oxidative Stress and Alzheimers Disease," Am. J. Clin. Nutr., vol. 71 (suppl), pp. 621S-629S (2000).

Clarke et al., Folate, Vitamin B12 and Serum Total Homocysteine Levels in Confirmed Alzheimers Disease, Arch. Neurol., vol. 55, pp. 1449-1455 (1998).

Clarke, R. et al., "Variability and Determinants of Total Homocysteine Concentrations in Plasma in an Elderly Population," Clin. Chem., vol. 44, No. 1, pp. 102-107 (1998).

Cohen, G., "The Brain on Fire?" Ann. Neurol., vol. 36, pp. 333-334 (1994).

Colton, C.A. et al., "Production of Superoxide Anions by a CNS Macrophase, the Microglia," FEBS Lett., vol. 223, pp. 284-288 (1987).

Cooper, A.J.L., "Glutathione in the Brain: Disorders of Glutathione Metabolism," in Rosenberg, R.N. et al. (eds.), *The Molecular and Genetic Basis of Neurological Disease*, Butterworth-Heinemann, Boston, pp. 1195-1230 (1997).

Diaz-Arrastia, R., "Homocysteine and Neurologic Disease," Arch. Neurol., vol. 57, pp. 1422-1427 (2000).

Drennan, C.L. et al., "How a Protein Binds $B_{12}$: A 3.0 Å X-Ray Structure of $B_{12}$-binding Domains of Methionine Synthase," Science, vol. 266, pp. 1669-1674 (1994).

Finkelstein, J.D., "Regulation of Homocysteine Metabolism," in Carmel, R. et al. *Homocysteine in Health and Disease*, $1^{st}$ ed., Cambridge University Press, Cambridge, pp. 92-99 (2001).

Finkelstein, J.D. et al., "Homocysteine," Int. J. Biochem. Cell Biol., vol. 32, No. 4, pp. 385-389 (2000).

Fischer, V.W. et al., "Altered Angioarchitecture in Selected Areas of Brains with Alzheimer's Disease," Acta. Neuropathologica, vol. 79, pp. 672-679 (1990).

Gottfries, C.G., "Pharmacological Treatment Strategies in Alzheimer Type Dementia," European Neuropsychopharmacology, vol. 1, No. 1, pp. 1-5 (1990).

Hankey, G.J. et al., "Homocysteine and Vascular Disease," Lancel, vol. 354, pp. 407-413 (1999).

Harman, D., "The Aging Process," Proc. Natl. Acad. Sci., vol. 78, pp. 7124-7128 (1981).

Henderson, A.S., "The Epidemiology of Alzheimer's Disease," Br. Med. Bull., vol. 34, No. 1, pp. 3-10 (1986).

IUPAC-IUB Commission on Biochemical Nomenclature, "The Nomenclature of Corrinoids," in *Biochemical Nomenclature and Related Documents*, $2^{nd}$ ed., Portland Press., 13 pages (1992).

Jacobsen, D.W. et al., Metabolism of Homocysteine by Vascular Cells and Tissues: Is the Transulfuration Pathway Active? (Abstract) Ir. J. Med. Sc., vol. 164, p. 10 (1995).

Katzman, R., "Alzheimer's Disease," N. Engl. J. Med., vol. 314, No. 15, pp. 964-973 (1986).

Keller, J.N. et al., "Oxidized Lipoproteins Increase Reactive Oxygen Species Formation in Microglia and Astrocyte Cell Lines," Brain Res., vol. 830, No. 1, pp. 10-15 (1999).

Kondo et al., "Nitrous Oxide Has Multiple Deleterious Effects on Cobalamin Metabolism and Causes Decreases in Activities of Both Mammalian Cobalamin Dependent Enzymes in Rats," J. Clin. Invest., vol. 67, pp. 1270-1283 (1981).

Kranich, O. et al., "Different Preferences in the Utilisation of Amino Acids for Glutathione Synthesis in Cultured Neurons and Astroglial Cells Derived from Rat Brain," Neurosci. Letters, vol. 219, pp. 211-214 (1996).

Kranich, O. et al., "Utilization of Cysteine and Cysteine Precursors for the Synthesis of Glutathione in Astroglial Cultures: Preference for Cystine," Glia, vol. 22, No. 1, pp. 11-18 (1998).

Kristensen et al., Serum Cobalamin and Methylmalonic Acid in Alzheimer Dementia, Acta. Neurol. Scand., vol. 87, pp. 475-481 (1993).

Lehmann et al., Identification of Cognitive Impairment in the Elderly; Homocysteine is an Early Marker, Geriatr. Cogn. Disord., vol. 10, pp. 12-20 (1999).

Lindenbaum et al. , "Neuropsychiatric Disorders Caused by Cobalamin Deficiency in the Absence of Anaemia or Macrocytosis," N. Engl. J. Med., vol. 318, pp. 1720-1728 (1998).

McCaddon, A. et al., "Analogues, Ageing and Aberrant Assimilation of Vitamin $B_{12}$ in Alzheimer's Disease," Dement. Geriatr. Cogn. Disord., vol. 12, pp. 133-137 (2001).

McCaddon, A. et al., "Homocysteine and Cognitive Decline in Healthy Elderly," Dement. Geriatr. Cogn. Disord., vol. 12, No. 5, pp. 309-313 (2001).

McCaddon, A. et al., "Nutritionally Independent $B_{12}$ Deficiency in Alzheimer's Disease," Arch. Neurol., vol. 57, No. 4, pp. 607-608 (2000).

McCaddon, A. et al., "Total Serum Homocysteine in Senile Dementia of Alzheimer Type," Int. J. Ger. Psych., vol. 13, pp. 235-239 (1998).

Morrison-Bogorad, M. et al., "Alzheimer's Disease Research Comes of Age: The Pace Accelerates," JAMA, vol. 277, pp. 837-840 (1997).

Mosharov, E. Et al., "The Quantitatively Important Relationship Between Homocysteine Metabolism and Glutathione Synthesis by the Transsulfuration Pathway and Its Regulation by Redox Changes," Biochemistry, vol. 39, pp. 13005-13011 (2000).

Mudd, S.H. et al., "Transulfuration in Mammals: Microassays and Tissue Distributions of Three Enzymes of the Pathway," J. Biol. Chem., vol. 240, No. 11, pp. 4382-4392 (1965).

Murphy, T.H. et al., "Glutamate Toxicity in a Neuronal Cell Line Involves Inhibition of Cystine Transport Leading to Oxidative Stress," Neuron, vol. 2, pp. 1547-1558 (1989).

Nilsson, K. et al., "The Plasma Homocysteine Concentration is Better than that of Serum Methylmalonic Acid as a Marker for Sociopsychological Performance in a Psychogeriatric Population," Clin. Chem., vol. 46, No. 5, pp. 691-696 (2000).

Nygard et al., "Total Plasma Homocysteine and Cardiovascular Risk Profile. The Hordaland Homocysteine Study," JAMA, vol. 274, No. 19, pp. 1526-1533 (1995).

Pezacka, E. et al., "Glutationylcobalamin as an Intermediate in the Formation of Cobalamin Coenzymes," Biochem. Biophys. Res. Commun., vol. 169, No. 2, pp. 443-450 (1990).

Pezacka, "Identification and Characterization of Two Enzymes Involved in the Intracellular Metabolism of Cobalamin," Biochem. Biophys. Acta., vol. 1157, pp. 167-177 (1993).

Ravindranath, Y. et al., "Low Glutathione Levels in Brain Regions of Aged Rats," Neurosci. Letters, vol. 101, pp. 187-190 (1989).

Regland, B. et al., "Vitamin $B_{12}$ Analogues, Homocysteine, Methylmalonic Acid, and Transcobalamins in the Study of Vitamin $B_{12}$ Deficiency in Primary Degenerative Dementia," Dementia, vol. 1, pp. 272-277 (1990).

Renvall, M.J. et al., "Nutritional Status of Free-Living Alzheimer's Patients," Am. J. Med. Sci., vol. 298, No. 1, pp. 20-27 (1989).

Riggs, K.M. et al., "Relations of Vitamin $B_{12}$, Vitamin $B_6$, Folate, and Homocysteine to Cognitive Performance in the Normative Aging Study," Am. J. Clin. Nutr., vol. 63, pp. 306-314 (1996).

Rosen, W.G. et al., "A New Rating Scale for Alzheimer's Disease," Am. J. Psychiatr., vol. 141, pp. 1356-1364 (1984).

Roses, A.D., "Apolipoprotein E Alleles as Risk Factors in Alzheimer's Disease," Ann. Rev. Med., vol. 47, pp. 387-400 (1996).

Sagara, J. et al., "Maintenance of Neuronal Glutathione by Glial Cells," J. Neurochem., vol. 61, pp. 1672-1676 (1993).

Schuchmann, S. et al., "Diminished Glutathione Levels Cuase Spontaneous and Mitochondria-Mediated Cell Death in Neurons from Trisomy 16 Mice: A Model of Down's Syndrome," J. Neurochem., vol. 74, pp. 1205-1206 (2000).

Selley, M.L. et al., "The Effect of Increased Concentrations of Homocysteine on the Concentration of (E)-4-hydroxy-2_nonanal in the Plasma and Cerebrospinal Fluid of Patients with Alzheimer's Disease," Neurobiol. Aging, May-Jun., vol. 23, No. 3, pp. 383-388 (2002).

Seshadri et al., Plasma Homocystine as a Risk Factor for Dementia and Alzheimer's Disease, N. Engl. J. Med., vol. 346(7), pp. 476-483 (2002).

Smith, M.A. et al., "Amyloid-β Deposition in Alzheimer Transgenic Mice is Associated with Oxidative Stress," J. Neurochem., vol. 70, No. 5, pp. 2212-2215 (1998).

Smith, M.A. et al., "Iron Accumulation in Alzheimer's Disease is a Source of Redox-Generated Free Radicals," Proc. Natl. Acad. Sci., vol. 94, pp. 9866-9868 (1997).

Smith, M.A. et al., "Oxidative Stress in Alzheimer's Disease," Biochem. Biophys. Acta., vol. 1502, No. 1, pp. 139-144 (2000).

Snowdon, D.A. et al., "Brain Infarction and the Clinical Expression of Alzheimer Disease: The Nun Study," JAMA, vol. 277 pp. 813-817 (1997).

Snowdon, D.A. et al., "Serum Folate and the Severity of Atrophy of the Neocortex in Alzheimer Disease: Findings from the Nun Study," Am. J. Clin. Nutr., vol. 71, pp. 993-998 (2000).

Stubbe, J., "Binding Site Revealed of Nature's Most Beautiful Cofactor," Science, vol. 266, pp. 1663-1664 (1994).

Taoka, S. et al., "Evidence for Heme-Mediated Redox Regulation of Human Cystathionine B-Synthase Activity," J. Biol. Chem., vol. 273, No. 39, pp. 25179-25184 (1998).

Ueland, P.M. et al., "Plasma Homocysteine, a Risk Factor for Fascular Disease: Plasma Lwevels in Health, Disease, and Drug Therapy," J. Lab. Clin. Med., vol. 114, pp. 473-501 (1989).

Uhlig, S. et al., "The Physiological Consequences of Glutathione Variations," Life Sci., vol. 51, No. 14, pp. 1083-1094 (1992).

Varadarajan, S. et al., "Methionine Residue 35 is Important in Amyloid b-peptide-associated Free Radical Oxidative Stress," Brain Res. Bulletin, vol. 50, No. 2, pp. 133-141 (1999).

Wang, J. et al., "Homocysteine Catabolism: Levels of 3 Enzymes in Cultured Human Vascular Endothelium and Their Relevance to Vascular Disease," (Abstract) Atherosclerosis, vol. 97, pp. 97-106 (1992).

White, A.R. et al., "Homocysteine Potentiates Copper- and Amyloid Beta Peptide-Mediated Toxicity in Primary Neuronal Cultures: Possible Risk Factors in the Alzheimer's-Type Neurodegenerative Pathways," J. Neurochem., vol. 76, No. 5, pp. 1509-1520 (2001).

Ariogul et al., "Vitamin B12, folate, homocysteine and dementia: are they really related?," Archives of Gerontology and Geriatrics, vol. 40, pp. 139-146 (2005).

Brigden, M.L., "Schilling Test still useful in pernicious anemia?" Postgraduate Medicine: Curbside Consults, vol. 106, No. 5, (Oct. 15, 1999).

Chiu, H.F.K., "Vitamin B12 Deficiency and Dementia" (International Journal of Geriatric Psychiatry, vol. 11, pp. 851-858 (1996).

Kelly, Gregory, "The Coenzyme Forms of Vitamin B12: Toward an Understanding of their Therapeutic Potential," Alternative Medicine Review, vol. 3, pp. 459-471 (1998).

McKenna, B. et al., "The induction of functional vitamin B12 deficiency in rats by exposure to nitrous oxide," Biochimica et Biophysica Acta, vol. 628, pp. 314 to 321 (1980).

Teunisse, S. et al., "Dementia and subnormal levels of vitamin B12: effects of replacement therapy on dementia," J. Neurol., vol. 243, pp. 522-529 (1996).

* cited by examiner

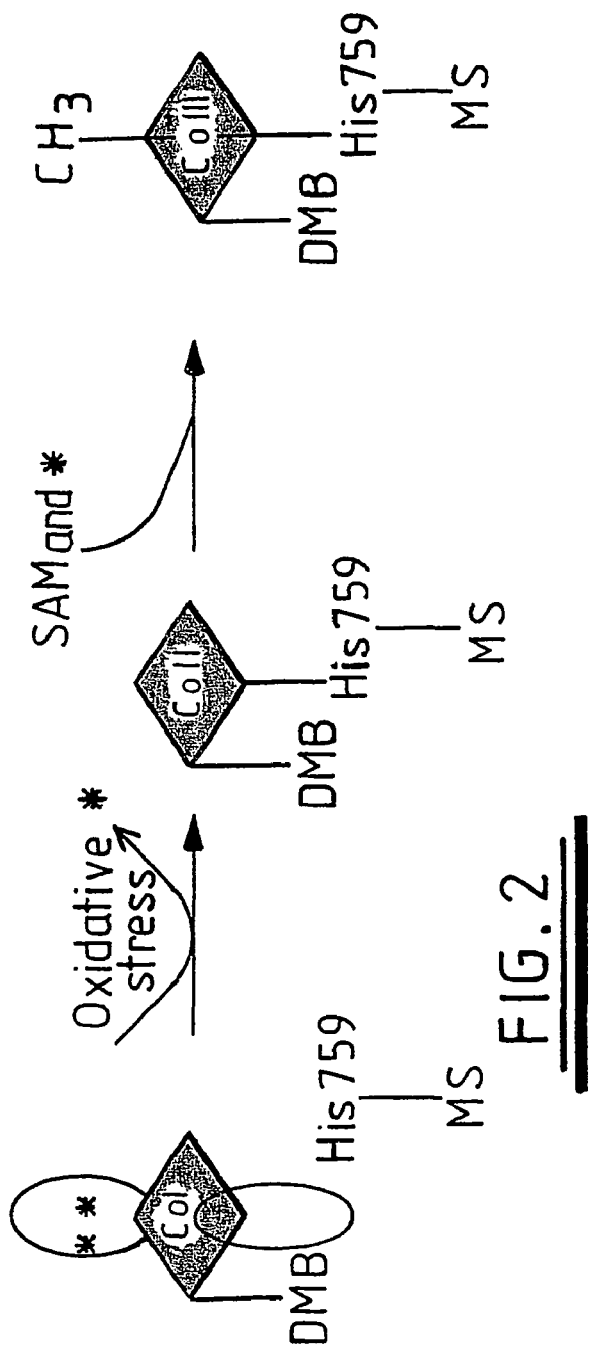
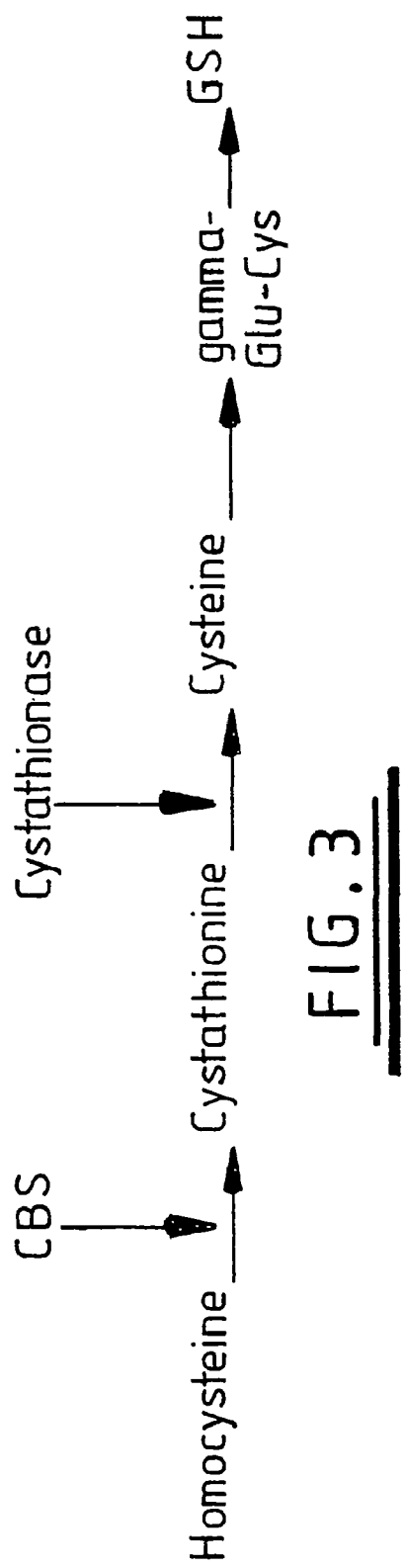
FIG. 2
FIG. 3

METHOD FOR TREATING OR PREVENTING A FUNCTIONAL VITAMIN B12 DEFICIENCY IN AN INDIVIDUAL AND MEDICAL COMPOSITIONS FOR USE IN SAID METHOD

This is the U.S. national stage of international application PCT/GB02/01843, international filing date Apr. 22, 2002. Priority is claimed under 35 U.S.C.§119(a)-(d) from GB application 0110336.5, filed Apr. 25, 2001; and also from GB application 0120363.7, filed Aug. 22, 2001.

The present invention relates to a method for treating or preventing a functional Vitamin $B_{12}$ deficiency in an individual and to medical compositions for use in said method. Such a functional $B_{12}$ deficiency may present as dementia, other neuropsychiatric abnormality and/or vascular disease.

Homocysteine is an intermediary amino acid derived from the breakdown of methionine. Its serum levels increase in individuals having folate, Vitamin $B_{12}$ (cobalamin) and pyridoxine deficiencies and genetically defective enzymes involved in its metabolism. Hyperhomocysteinemia, the term given to raised blood concentration of homocysteine, is associated with cardiovascular, peripheral vascular, and cerebrovascular disease. A potential role for hyperhomocysteinemia in the aetiology of Alzheimer's Disease (AD) has been postulated. Support for this comes from several recent investigations (1, 2, 3, 4). Perhaps the most compelling of these is the case control study of histologically confirmed AD patients and age-matched controls which demonstrated a 4.6-fold increased risk of having AD in individuals with serum homocysteine>14 micromol/L compared to those with serum homocysteine of less than 11 micromol/L (2). Recently, an important prospective observational study of a cohort of 1092 elderly subjects in the Framingham Study has greatly strengthened the evidence for an association between plasma homocysteine level and dementia (4). In this study, an elevated plasma total homocysteine level at base line was an independent predictor of the development of clinical dementia, most cases of which were caused by AD. After a median of eight years of follow-up, dementia had developed in 111 subjects. The risk of AD was almost doubled for those with the highest plasma homocysteine levels; a 5 µmol increment in plasma homocysteine increased the risk of AD by 40%. The aforementioned investigations demonstrate that homocysteine also correlates with cognitive scores in AD and vascular dementia. Furthermore, it appears to be an independent predictor of cognitive decline in healthy elderly (5).

A tissue deficiency of cobalamin also results in elevated serum methylmalonic acid. Raised levels of methylmalonic acid have also been demonstrated in serum of patients with AD suggesting that they suffer from metabolic cobalamin deficiency (6). Elevated serum homocysteine and methylmalonic acid have also been associated with neurological and psychiatric signs and symptoms (e.g. impaired vibration sense, paraesthesia, impaired position sense, impaired touch or pain perception, "diabetic" neuropathy, ataxia, abnormal gait, decreased reflexes and muscle strength, weakness, fatigue) and various neurological and psychiatric disorders, including chronic fatigue syndrome, depressive illness and multiple sclerosis indicating that cobalamin deficiency is commonly associated with such disorders (7). Interestingly, the usual haematological signs of cobalamin deficiency including anaemia and macrocytosis are commonly absent in these patients.

Previously, individuals with occlusive vascular disease or AD have been treated with folic acid, a folate or a derivative thereof and, optionally, vitamin $B_{12}$ (U.S. Pat. No. 6,127,370. Smith et al.,). However, the administration of such compounds to patients suffering from hyperhomocysteinemia is not always found to fully alleviate the symptoms associated with such raised levels of homocysteine. The evidence referred to above (1, 2, 3, 4, 5) clearly shows that there is metabolic evidence for $B_{12}$ deficiency in association with AD vascular disease, age-related cognitive decline and various neuropsychiatric disorders, although the exact mechanism underlying these associations has been unclear until now.

The Inventor herein demonstrates that in patients with AD metabolic evidence of $B_{12}$/folate deficiency, reflected by hyperhomocysteinemia, arises independently of nutritional status (as determined by body mass index) and is not associated with haematological abnormalities, which would occur with malabsorption of $B_{12}$ or folate. Furthermore, the deficiency is not associated with low levels of red blood cell folate, again suggesting normal intake/absorption, but is associated with elevated blood levels of cysteine, demonstrating increased transsulfuration of homocysteine. This identifies the biochemical locus of the hyperhomocysteinemia as arising from a remethylation defect with a compensatory increased flux via the transsulfuration pathway. Additionally, blood levels of glutathione, a key antioxidant, are inversely associated with disease severity.

Taken together, the aforementioned findings show that patients with AD have a "functional" vitamin $B_{12}$ deficiency, rather than a "classical" deficiency arising from impaired absorption of the vitamin (e.g. pernicious anaemia). Recently, further supporting evidence for a functional vitamin $B_{12}$ deficiency in AD patients has been published (8). This clearly shows a relationship between oxidative stress and elevated concentration of homocysteine in plasma and cerebrospinal fluid of patients with AD. Vascular endothelium and neuronal tissue are particularly sensitive to oxidative stress. The effects of such stress on the intracellular metabolism of vitamin $B_{12}$ result in the functional deficiency. Both endothelium and neurons lack an intact transsulfuration pathway, impairing their ability to synthesize the antioxidant gluthathione. Both tissues also lack any alternative means to remethylate homocysteine via betaine, namely betaine:homocysteine methyltransferase (9). Increased cellular export of homocysteine is therefore the only route available to these tissues when the methionine synthase reaction is impaired by oxidative stress.

The "functional" vitamin $B_{12}$ deficiency that arises due to the effects of oxidative stress on $B_{12}$ metabolism as recognized by the Inventor may be revealed by elevated blood levels of homocysteine and/or methylmalonic acid, and/or low levels of total serum $B_{12}$ and/or low levels of the $B_{12}$ carrier protein holo-transcobalamin. A functional vitamin $B_{12}$ deficiency occurs in the absence of any demonstrable malabsorption of the vitamin and, usually, in the absence of any associated haematological abnormalities. The recognition of this functional deficiency has enabled the Inventor to arrive at a method and composition for treating and/or preventing symptoms associated therewith.

It is an object of the present invention to provide an improved method of treating or preventing a functional Vitamin $B_{12}$ deficiency in an individual which may eventually present as dementia, other neuropsychiatric abnormality and/or vascular disease. Such symptoms are brought about as a consequence of oxidative stress on biochemical pathways.

A further object of the present invention is to provide an improved medical composition for use in treating or preventing a functional Vitamin $B_{12}$ deficiency in an individual which may eventually present as dementia, other neuropsychiatric abnormality and/or vascular disease.

Accordingly, a first aspect of the present invention provides a method for treating or preventing a functional Vitamin $B_{12}$ deficiency in an individual that occurs due to a disorder in the intracellular processing of Vitamin $B_{12}$ rather than the malabsorption thereof, the symptoms of said functional Vitamin $B_{12}$ deficiency including elevated blood levels of homocysteine and/or methylmalonic acid, and/or low levels of total serum $B_{12}$ and/or low levels of holo-transcobalamin, the method composing administering to the individual a therapeutically effective amount of a medical composition that directly or indirectly supplies a cobalt-sulphur bond in the upper β-axial ligand of an intracellular cobalamin molecule thereby facilitating intracellular processing of cobalamins.

A second aspect of the present invention provides a medical composition for use in the treatment or prevention of a functional Vitamin $B_{12}$ deficiency in an individual that occurs due to a disorder in the intracellular processing of Vitamin $B_{12}$ rather than the malabsorption thereof, the symptoms of said functional Vitamin $B_{12}$ deficiency including elevated blood levels of homocysteine and/or methylmalonic acid, and/or low levels of total serum $B_{12}$ and/or low levels of holo-transcobalamin the composition comprising a compound or a combination of compounds that directly or indirectly supplies a cobalt-sulphur bond in the upper β-axial ligand of an intracellular cobalamin molecule thereby facilitating intracellular processing of cobalamins.

The cobalt-sulphur bond in the upper β-axial ligand of the cobalamin molecule may be provided directly by administering a therapeutic amount of a thiolatocobalamin that already contains the cobalt-sulphur bond or indirectly by the co-administration of Vitamin $B_{12}$ (cyanocobalamin) or a derivative thereof with a sulphur containing molecule, such as glutathione, or a precursor thereof.

The medical composition may facilitate intracellular processing of cobalamin in tissues that suffer from oxidative stress, in particular neuronal tissue and vascular endothelium.

Any suitable thiolatocobalamin may be provided to supply directly the cobalt-sulphur bond, including the preferred compound glutathionylcobalamin (CAS: 129128-04-7) and related sulphur-containing cobalamins having the generic form Coα[α-(5,6-Dimethylbenzimidazolyl)]-Coβ-ligandyl) cobamide, in which the upper β-axial ligand group is co-ordinated to the cobamide by a sulphur-cobalt bond, such as (but not limited to) sulphitocobalamin (syn-sulfitocobalamin; CAS: 15671-27-9), cysteinylcobalamin (CAS: 60659-91-8), cyclohexylthiolatocobalamin and pentafluorophenylthiolatocobalamin.

To this end, a third aspect of the present invention provides a method for treating or preventing a functional Vitamin $B_{12}$ deficiency in an individual that occurs due to a disorder in the intracellular processing of Vitamin $B_{12}$ rather than the malabsorption thereof, the symptoms of said functional Vitamin $B_{12}$ deficiency including elevated blood levels of homocysteine and/or methylmalonic acid, and/or low levels of total serum $B_{12}$ and/or low levels of holo-transcobalamin, the method comprising administering to the individual a therapeutically effective amount of a thiolatocobalamin.

A fourth aspect provides a medical composition for use in the treatment or prevention of a functional Vitamin $B_{12}$ deficiency in an individual that occurs due to a disorder in the intracellular processing of Vitamin $B_{12}$ rather than the malabsorption thereof, the symptoms of said functional Vitamin $B_{12}$ deficiency including elevated blood levels of homocysteine and/or methylmalonic acid, and/or low levels of total serum $B_{12}$ and/or low levels of holo-transcobalamin, the medical composition comprising a thiolatocobalamin.

A fifth aspect of the present invention provides a method for treating or preventing a functional Vitamin $B_{12}$ deficiency in an individual that occurs due to a disorder in the intracellular processing of Vitamin $B_{12}$ rather than the malabsorption thereof, the symptoms of said functional Vitamin $B_{12}$ deficiency including elevated blood levels of homocysteine and/or methylmalonic acid, and/or low levels of total serum $B_{12}$ and/or low levels of holo-transcobalamin comprising administering to the individual a therapeutically effective amount of Vitamin $B_{12}$ or a derivative thereof selected from the group consisting of hydroxocobalamin, methylcobalamin and adenosyl cobalamin in conjunction with a therapeutically effective amount of glutathione and/or a precursor for the compound glutathione, the precursors being selected from the group consisting of N-acetyl cysteine, L-taurine, L-methionine, S-adenosyl methionine, α-lipoic acid, L-α oxothiazolidine-4-carboxylate, L-γ-glutamyl-L-cysteinylglycyl ethyl ester, γ-glutamyl cysteine and cysteinylglycine to facilitate intracellular processing of cobalamin.

A sixth aspect of the present invention provides a medical composition for use in the treatment or prevention of a functional Vitamin $B_{12}$ deficiency in an individual that occurs due to a disorder in the intracellular processing of Vitamin $B_{12}$ rather than the malabsorption thereof, the symptoms of said functional Vitamin $B_{12}$ deficiency including elevated blood levels of homocysteine and/or methylmalonic acid, and/or low levels of total serum $B_{12}$ and/or low levels of holo-transcobalamin, the composition comprising Vitamin $B_{12}$ or a derivative thereof selected from the group consisting of hydroxocobalamin, methylcobalamin and adenosyl cobalamin in combination with glutathione and/or a precursor for the compound glutathione, the precursors being selected from the group consisting of N-acetyl cysteine, L-taurine, L-methionine, S-adenosyl methionine, α-lipoic acid, L-α oxothiazolidine-4-carboxylate, L-γ-glutamyl-L-cysteinylglycyl ethyl ester, γ-glutamyl cysteine and cysteinylglycine to faciliate intracellular processing of cobalamin.

The medical composition according to this aspect of the present invention preferably comprises Vitamin $B_{12}$, or a derivative thereof, and N-acetyl cysteine or α-lipoic acid The medical composition is particularly suitable for facilitating processing of cobalamin in neuronal tissues and vascular endothelium that are vulnerable to the effects of oxidative stress.

It is to be appreciated that a combined treatment of a thiolatocobalamin, glutathione, a glutathione precursor and/or cobalamin may also be administered to the individual.

Additionally, the medical composition may be co-administered with additional compounds to assist in their therapeutic action against neuropsychiatric and/or vascular disease. For example, the composition may be co-administered with other factors involved in the metabolism of homocysteine, such as folate and/or vitamin B6. The compositions may also be co-administered with any methyl-donor, such as, but not limited to, folic acid, methyl-folate, S-adenosylmethionine, betaine, choline and carnitine.

Any appropriate mode of administration may be used, such as (but not limited to) oral, sublingual, intravenous and parenteral administration.

For a better understanding of the present invention and to show more clearly how it may be carried into effect reference will now be made to the following Examples in which Example 1 investigates the relationship between homocysteine, haematological indices and dementia duration in patients with clinically diagnosed Alzheimers Disease (AD), Example 2 investigates the effects of the co-administration of a glutathione precursor (N-acetyl cysteine or α-lipoic acid)

and hydroxocobalamin (a derivative of Vitamin $B_{12}$) to patients with a functional Vitamin $B_{12}$ deficiency and suffering from a neuropsychiatric abnormality, and Example 3 provides evidence for a functional Vitamin $B_{12}$ deficiency in patients with DSM-IV criteria for primary degenerative dementia of Alzheimer type and investigates its relationship with cognitive score, and with reference to the accompanying drawings, in which:—

FIG. 2 illustrates the re-activation of cob(II)-alamin by methionine synthase reductase;

FIG. 3 illustrates the transulfuration pathway wherein homocysteine is metabolized to glutathione (GSH);

Figure 1:
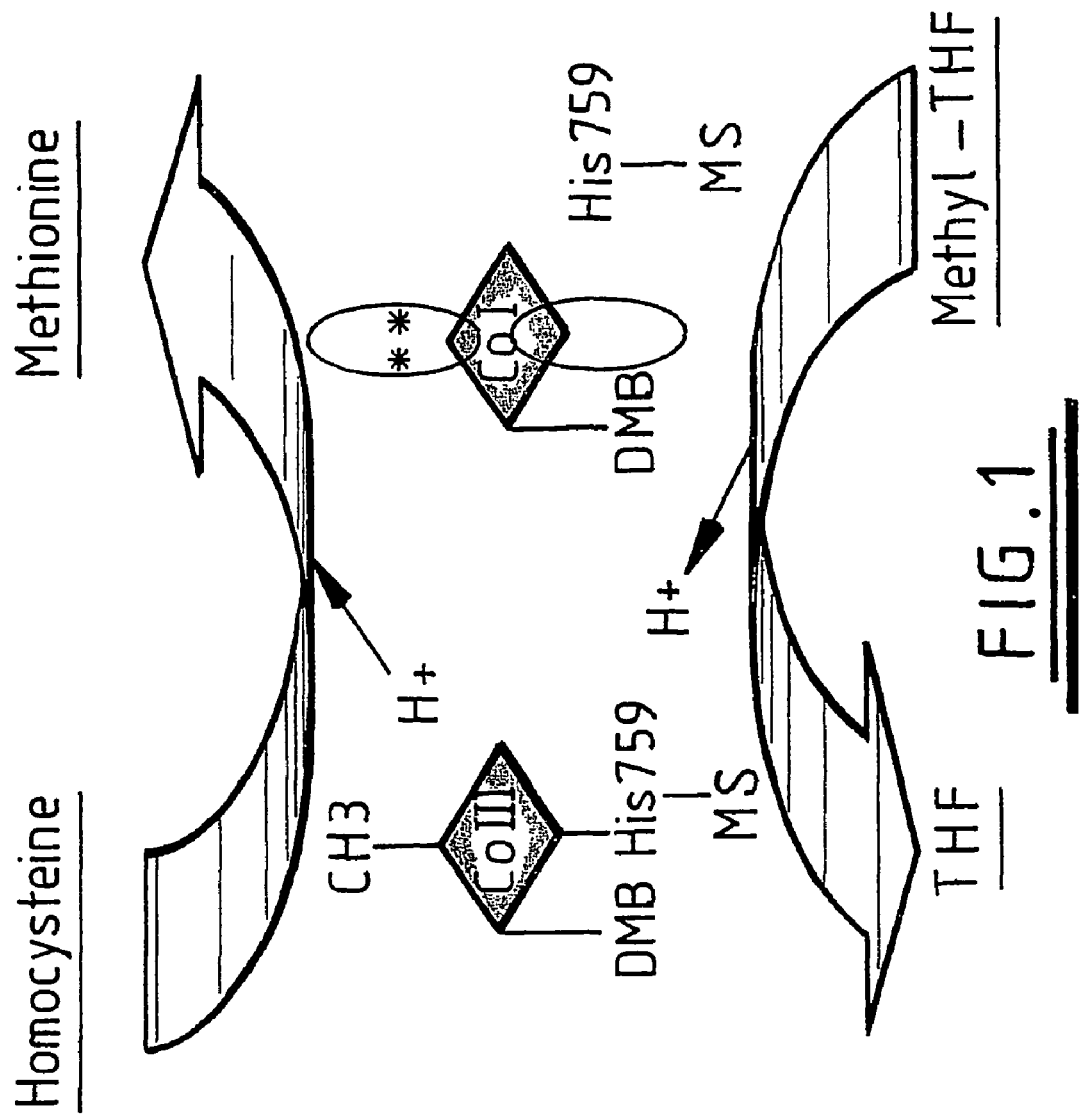
FIG. 1 illustrates the primary activation cycle of the methionine synthase reaction.

The present invention relates to the recognition of the implication of hyperhomocysteinemia in a pathogenic mechanism common to the development of AD, vascular disease and aging. In particular, it has been found that this mechanism relates to the influence of ambient redox status on key enzymes of homocysteine metabolism. An inevitable implication of this mechanism is aberrant intraneuronal and intra-endothelial processing of cobalamins by the β-ligand transferase and cobalamin reductase enzymes. Pharmaceutical preparations of cobalamin in current use, such as hydroxocobalamin (CAS: 13422-51-0), cyanocobalamin ("Vitamin $B_{12}$" CAS: 68-19-9), methylcobalamin (CAS: 13422-55-4) and adenosyl cobalamin ("Coenzyme B12" CAS: 13870-90-1) cannot be utilised by neurones or vascular endothelium due to their lack of a crucial Co—S bond resulting in this particular metabolic block. However, the administration of glutathionylcobalamin, or any related cobalamins of the generic form Coα-[α(5,6-Dimethylbenzimidazolyl)]-Coβ-ligandyl) cobamide, in which the upper β-axial ligand group is coordinated to the cobamide by a sulphur-cobalt bond (i.e. thiolatocobalamins) can overcome this redox-related metabolic block. The presence of a cobalt-sulphur bond in the upper β-axial ligand of the cobalamin molecule is an essential prerequisite for intracellular processing of cobalamins. Neurones and vascular endothelium are unable to generate this bond under conditions of oxidative stress. Accordingly, the method and compositions provided by the present invention ensure the presence of a cobalt-sulphur bond in neuronal or vascular endothelium cobalamin, either directly by administering a thiolatocobalamin or indirectly by co-administering currently available forms of Vitamin $B_{12}$ together with the sulphur-containing molecule glutathione or one of its precursors, such as N-acetyl cysteine (NAC) or α-lipoic acid.

In order to be able to determine the effects of high levels of homocysteine in the body and to understand the effects of oxidative stress on homocysteine levels and cobalamin metabolism, it is important to understand the roles of these substances in the body. Homocysteine is a key junction metabolite in methionine metabolism. Homocysteine may be methylated by means of the enzyme methionine synthase (MS) or transsulfurated by the enzyme cystathionine β-synthase (CBS) leading to cystathionine. The latter is subsequently converted to cysteine, a precursor of reduced glutathione (GSH).

Studies with purified mammalian MS and CBS have revealed that these junction enzymes are sensitive to oxidation, suggesting that the redox regulation of these pathways may be physiologically significant (10). Approximately one half of the intracellular GSH pool in human liver cells is derived from homocysteine via the transsulfuration pathway. The redox sensitivity of these pathways can be rationalized as an autocorrective response resulting in increased GSH synthesis in cells challenged by oxidative stress. The transsulfuration pathway is therefore important for the maintenance of the intracellular GSH pool, and the regulation of this pathway is altered under conditions of oxidative stress.

There is already considerable evidence implicating oxidative stress in AD (11). The brain is especially vulnerable to oxidative stress for several reasons. It has high concentrations of catalytic iron and a relatively low level of antioxidant enzymes compared to other tissues. It is rich in membrane lipids and polyunsaturated fatty acids amenable to peroxidation and has high energy demands met almost exclusively by oxidative phosphorylation. Oxidative damage, although a common finding in the aging brain, is more severe in patients with AD.

Furthermore, oxidative stress has recently been associated with cognitive decline even in healthy elderly. A study of 1166 high cognitive functioning subjects aged 60 to 70 demonstrated that increased oxidative stress, or antioxidant deficiency, are risk factors for cognitive decline with increasing age (12).

There are three ways in which oxidative stress can Compromise cobalamin (vitamin $B_{12}$) metabolism in dementia or vascular disease. Firstly, in the normal methylation cycle (as illustrated in FIG. 1 of the accompanying drawings) the thiolate of homocysteine reacts with the methyl ($CH_3$) group of MS-bound methylcobalamin to produce methionine and four-coordinate cob(I)alamin. Histidine (His759 from MS) forms the lower axial cobalt ligand, replacing dimethylbenzimidazole (DMB) that is now in a hydrophobic methionine synthase pocket (*=electron). Cob(I)alamin, a highly reactive cobalamin species, then reacts with an activated form of methylTHF to generate free THF and regenerate methylcobalamin.

Methylcobalamin cycles, via a protonation and deprotonation, between enzyme bound Cob(III) alamin and free Cob(I) alamin states, as illustrated in FIG. 1. S-adenosylmethionine (SAM) and an electron source (*) regenerate the active form of MS when cob(I)alamin is abnormally oxidised to cob(II) alamin (see FIG. 2). In the other human cobalamin dependent enzyme system involving methymalonyl-CoA mutase (MCM), the upper axial carbon-cobalt bond splits heterolytically rather than homolytically and the cobalt atom remains in the relatively inert cob(II)alamin form. Oxidative stress impairs MS function whilst relatively sparing mutase activity. Hence, a consequence of oxidative stress is to increase homocysteine levels. Oxidative damage is also associated with the formation of cobalamin analogues which have been demonstrated in vivo (13) and, more recently, have been observed in AD (14).

Figure 4:
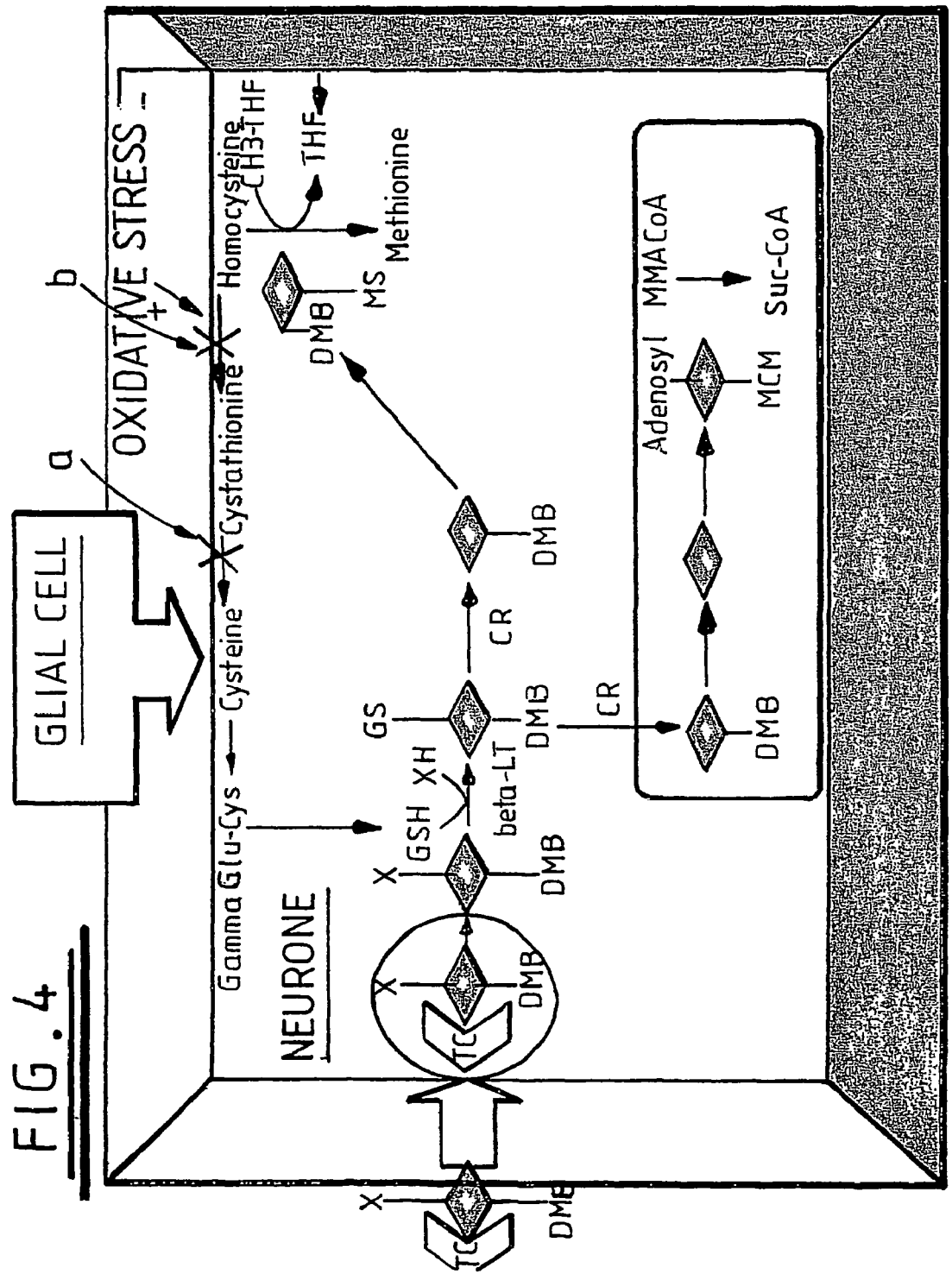
FIG. 4 illustrates the effect of oxidative stress on homocysteine flux and its implication for neuronal and vascular endothelial cobalamin metabolism.

Secondly, oxidative stress can increase homocysteine flux via the transsulfuration pathway as a consequence of its stimulation of cystathionine β-synthase (CBS) activity (see FIG. 3). The redox sensitivity of CBS probably represents an autocorrective response resulting in increased intracellular levels of glutathione (GSH) in cells challenged by oxidative stress (10). However, the absence of cystathionase, and hence low glutathione, in neurones makes these cells particularly prone to such challenges (FIG. 4,*a*) as does the low activity of CBS in vascular endothelial cells (FIG. 4,*b*).

Thirdly, oxidative stress has a further serious implication for cobalamin metabolism within neurones and vascular endothelial cells. The key enzymes involved in the processing of various forms of cobalamin following their delivery to the cell by transcobalamin (TC) have been delineated (15), see FIG. 4. Different β-ligand forms of cobalamin bound to TC are internalised and converted to methyl-and adenosyl-forms. Methylcobalamin is formed in the reaction catalysed by methionine synthase as an intermediate of the methyl transfer reaction provided that cobalamin is made available in an appropriate redox form (cob(I)alamin or cob(II)alamin).

Glutathionylcobalamm (GS-Cbl), a naturally occurring intracellular form of cobalamin, is a proximal precursor in the biosynthesis of cobalamin enzymes (15). β-ligand transferase (beta-LT) is a cytosolic enzyme utilizing FAD, NADPH, and reduced glutathione (GSH). Although this study utilised CN-cobalamin, it is highly probable that CN-Cbl beta-ligand transferase catalyses a general beta-ligand elimination reaction of newly internalized cobalamins with GS-Cbl being the obligate intracellular intermediate.

The role of the enzyme cob(III)alamin reductase (CR) has also been studied (15). This utilises aq-Cbl, GS-Cbl and $HSO_3$-Cbl as substrates, but preferentially the latter two. Little or no reductase activity was observed with Me-Cbl, Ado-Cbl or CN-Cbl as substrates. The product of this reaction, cob(II)alamin, becomes bound to cytosolic MS (or, alternatively, is further reduced to cob(I)alamin in mitochondria, followed by conversion to adenosylcobalamin, a co-factor for methylmalonylCoA mutase), see FIG. 4.

Hence, intracellular processing of cobalamin requires reduced glutathione (GSH) for the formation of the obligate intracellular intermediate form of cobalamin (GS-Cbl) which possesses an essential cobalt-sulphur bond. GSH is a ubiquitous tripeptide consisting of glycine, cysteine and glutamate. It participates in many vital cellular functions, including the synthesis of proteins, enzyme activity, metabolism, and protection against oxidative stress. Neuronal and vascular endothelial GSH synthesis depends on the presence of its precursors. Glutamate and glycine are synthesised via several metabolic pathways, and therefore their influence on GSH synthesis is limited. However, neuronal and endothelial GSH levels are strongly affected by the supply of cysteine or its oxidised form cystine. Cysteine is rapidly oxidised to cystine, which is extracellularly predominant. Cystine is taken up by glial cells via the cystine/glutamate antiporter and subsequently reduced to cysteine. Neurones are not able to reduce cystine to cysteine nor convert cystathionine to cysteine (see FIG. 4,a) and therefore depend upon glial cysteine to preserve their GSH level. Cysteine has been confirmed as a rate limiting precursor for neuronal GSH synthesis. Consequently, glutathione content of neurones is very low. Similarly, vascular endothelium also lacks the ability to synthesize endogenous cysteine from homocysteine (see FIG. 4,b).

The absence of an increase in production of reduced glutathione by means of the transsulfuration pathway in neurones and vascular endothelium under conditions of oxidative stress results in reduced glutathione being rapidly depleted in these tissues. Since this is an essential precursor of the obligate intracellular cobalamin intermediate glutathionylcobalamin (GS-Cbl), neuronal and vascular endothelial cobalamin metabolism is compromised. Homocysteine levels will therefore increase even further in a harmful "feed forward" cascade. The Inventor has realized that only the presence of a cobalt-sulphur bond in neuronal and endothelial cobalamins will circumvent this block and reduce homocysteine levels in these tissues and that this can be achieved by either the direct administration of a thiolatocobalamin, such as synthetic glutathionyl cobalamin (Method of manufacture described in, for example, GB 945772) or indirectly by the co-administration of Vitamin $B_{12}$ and glutathione, or one of the precursors such as, for example, N-acetyl cysteine (CAS: 616-91-1), glycine (CAS: 56-40-6), L-glutamine (CAS: 56-85-9), L-taurine (CAS: 107-35-7), L-methionine (CAS: 63-68-3), α-lipoic acid (CAS: 6246-4), cysteinylglycine (CAS: 19246-18-5) and S-adenosyl methionine (CAS: 29908-03-0).

EXAMPLE 1

The relationship between homocysteine, haematological indices, and dementia duration in patients with clinically diagnosed AD was investigated. It was hypothesized that if metabolic evidence of vitamin B12 deficiency arose by "classical" $B_{12}$ malabsorption then increasing duration of dementia should be associated with the development of haematological abnormalities.

Patients were recruited from the Wrexham Maelor Psychogeriatric Assessment Service with features compatible with DSM-IV criteria for primary degenerative dementia of Alzheimer-type. Controls were healthy cognitively intact age and sex matched elderly volunteers from a group General Practice in a comparable semi-rural area of predominantly lower socio-economic class. Patients or controls receiving vitamin $B_{12}$ or folate supplements, or taking medication known to influence homocysteine were excluded.

Cognitive scores (Mini Metal State Examination (MMSE) and the cognitive component of the Alzheimer Disease Assessment Scale (ADAS-Cog)) were recorded for cases and controls (16, 17).

Body mass index (BMI) was determined from height and weight measured at assessment. Duration of dementia in months was determined from records wherever possible, or alternatively from next of kin or carers.

Non-fasting blood samples were taken for full blood count, red cell folate (RCF), creatinine, $B_{12}$, folate, and homocysteine assays. Separation and freezing were performed within one hour of venepuncture.

An automated cell counter was used to measure haemoglobin (Hb) concentration, and MCV (*Coulter Gen-S*, Beckman Coulter, High Wycombe, Bucks, UK). The red cell distribution width (RDW) was mathematically derived from the frequency over red cell volume histogram on the same instrument. A broad curve, resulting from cells with wide range of cell volume, will yield a raised RDW. An automated biochemistry analyser was used to analyse creatinine (*Synchron LX*-20 *analyser*, Beckman Coulter, High Wycombe, Bucks, UK) and an automated chemiluminescence analyser was used to measure folate, vitamin $B_{12}$ and RCF (*ACS*;180 *SE*, Bayer plc, Newbury, Berks UK) using the manufacturers' recommended protocols. Homocysteine was assayed with an automated HPLC system (DS30 *Hcy Analyser*, Drew Scientific Group plc, Barrow in Furness, Cumbria, UK). All forms of homocysteine were assayed including protein bound, non-protein bound, free forms both oxidized (dimer and mixed disulphides) and reduced. Values presented therefore always refer to "total" plasma levels.

Comparisons between groups were performed using the Mann-Whitney U test. (*Statistica for Windows v*5.5, StatSoft, Inc., Tulsa, Okla.). Median values are presented with inter-quartile ranges. A generalized linear model, using a linear link function, was used to assess relationships between variables. Regression parameters are presented with their 95% confidence intervals.

Forty-four patients and fifty-five control subjects were recruited to the study. There were no significant differences between the two groups regarding age, sex, BMI, and creatinine. Patients scored significantly worse on scores of cognitive function (p<0.0001), see Table 1 below.

TABLE 1

|  | Age | Sex | BMI | Creatinine | MMSE | ADAS-Cog |
|---|---|---|---|---|---|---|
| Controls (n = 55) | 79 | 22 M 33 F | 24.1 | 84 | 28 | 9 |
|  | (72-86) |  | (22.1-28.4) | (72-102) | (27-29) | (7-12) |
| Patients (n = 44) | 79 | 14 M 30 F | 24.5 | 85 | 17 | 32 |
|  | (75-84) |  | (21.8-27.6) | (72-115) | (13-21) | (24-40) |

There were no significant differences for Hb, WBC, platelets, MCV, RDW, $B_{12}$, or RCF between groups. Patients had significantly higher serum homocysteine (p=0.0008) and lower serum folate (p=0.02) than controls, see Table 2 below.

TABLE 2

|  | Controls | Patients |
|---|---|---|
| Hb (g/dl) | 13.4 (12.5-14.4) | 12.8 (12-14.0) |
| WBC ($\times 10^9$/l) | 6.9 (6.1-8.0) | 6.9 (6.0-8.2) |
| Platelets ($\times 10^9$/l) | 219 (184-277) | 219 (181-271) |
| MCV (fl) | 90.6 (87.8-94.0) | 90.0 (87.7-93.5) |
| RDW | 13.4 (12.9-14.0) | 13.6 (12.9-14.4) |
| $B_{12}$ (ng/l) | 324 (291-445) | 328 (268-421) |
| Folate (µg/l) | 11.1 (8.2-14.5) | 9.1 (6.4-11.7) |
| RCF (µg/l) | 332 (272-429) | 282 (243-399) |
| Homocysteine (µmol/l) | 9.8 (8.5-12.5) | 12.2 (9.4-15.7) |

A generalized linear model was used to determine the relationship between haematological variables and disease duration in the patient group. Gender was included as an additional variable.

Increasing duration of dementia was associated with a slight decline in haemoglobin (Hb=13.67−0.023 (−0.003 to −0.04)×duration+0.20 (−0.2 to 0.61)×gender; p=0.02), and platelet count (Platelets=246.6−0.96 (−1.79 to −0.13)×duration−5.3 (−22.2 to 11.7)×gender; p=0.03).

There was no relationship between disease duration and WBC, MCV, or RDW. Homocysteine, but not B vitamins, declined with increasing dementia duration (Homocysteine=16.4−0.085 (−0.17 to −0.002)×duration+1.95 (0.25 to 3.65)×gender; p=0.048).

This study confirms earlier observations of increased plasma homocysteine and reduced serum folate levels in patients with clinically diagnosed AD (3;4). Haemoglobin and platelet counts fell only slightly with increasing dementia duration, and there were no other changes in haematological indices; macrocytosis and RDW in particular were not related to disease duration, and no patients were anaemic.

AD patients therefore exhibit a "functional" $B_{12}$/folate deficiency, but in the absence of "classical" haematological indicators. Low serum folate, but normal red cell folate, in AD suggests that these patients are in negative folate balance, i.e. more folate has been catabolized than absorbed.

Lindenbaum et al (7) suggested that neuropsychiatric features of B vitamin deficiency precede haematological changes. However, the current data clearly shows that this is not the case in patients with AD. It demonstrates that the association between B vitamin deficiency and AD is due to an entirely different pathogenic mechanism from that associated with classical malnutrition or malabsorption-related syndromes and their related haematological sequelae. A "functional" cerebral $B_{12}$/folate deficiency exists in AD with relative sparing of haematopoietic tissue.

It is submitted that the effects of AD-related cerebral oxidative stress on vitamin $B_{12}$ metabolism account for this "functional" deficiency. Oxidative stress augments the oxidation of an intermediate form of vitamin $B_{12}$ generated in the methionine synthase reaction, thereby impairing the metabolism of homocysteine. Furthermore, oxidative stress compromises the intraneuronal reduction of vitamin $B_{12}$ to its metabolically active state. Since this stress is confined to brain tissue, haematopoietic methionine synthase activity is relatively unaffected, thus explaining the absence of anaemia and macrocytosis in these patients.

The present data also shows that the relationship between AD and folate status reflects excess folate catabolism. Methionine synthase inactivation results in folate being trapped in the methyltetrahydrofolate form. It is unavailable for polyglutamation, a necessary prerequisite for cellular retention, and is released from cells. It is subsequently excreted in the urine, eventually resulting in folate depletion. Haematopoietic tissue is spared in this process, explaining the normal red cell folate values and absent anaemia.

Vitamin $B_{12}$ (cyanocobalamin), adenosylcobalamin and methylcobalamin have a cobalt-carbon bond at the β-axial position and hydroxocobalamin has a cobalt-oxygen bond. Hence, these commonly used pharmaceutical derivatives cannot be used by neuronal tissues under conditions of oxidative stress due to reduced supplies of intracellular glutathione necessary to convert these cobalt bonds to cobalt-sulphur bonds and hence, to a metabolically active form. Glutathionylcobalamin, or related thiolatocobalamins, in which the upper β-axial ligand of the cobalamin molecule already possess a sulphur-cobalt bond, can overcome this redox-related metabolic block and thereby reduce the symptoms of oxidative stress on neuronal tissues. The co-administration of Vitamin $B_{12}$ with glutathione, or a precursor thereof, can also overcome this metabolic block by providing the requisite cobalt-sulphur bond. The provision of a cobalt-sulphur bond at the upper β-axial ligand should be of particular utility in the treatment and/or prevention of neuropsychiatric and/or vascular disorders associated with metabolic or other evidence of $B_{12}$ deficiency, especially those in which the classical haematological signs of anaemia and macrocytosis are absent or non-significant, as demonstrated by the Example given above. Anaemia is absent in such situations due to the bone-marrow being able to metabolize homocysteine and thus, unlike neuronal tissues, has sufficient levels of glutathione to protect against oxidative stress and generate the cobalt-sulphur bond of the obligate intracellular cobalamin intermediate, glutathionylcobalamin.

EXAMPLE 2

The effect of generating a cobalt-sulphur bond by the co-administration of hydroxocobalamin and a glutathione precursor (N-acetyl cysteine or α-lipoic acid) on the symptoms of seven patients suffering from neuropsychiatric abnormalities was investigated.

Patient 1:

In 1994, a 78 year old woman visited her General Practitioner (GP) with a several month history of tiredness, lethargy, shakiness, a disturbed sleep pattern, depression and malaise. A Physician had assessed her in 1991 with regard to her malaise when she also complained of feeling miserable, tearful and breathless, with the occasional sensation of a lump in her throat. However, no significant features were found on clinical examination and it was felt that her conditions were anxiety-related. The patient's biochemical and haematological investigations were entirely normal and the patient was discharged. Vitamin B12 and folate levels were not measured at that tine.

On examination in 1994, there were still no obvious clinical abnormalities, other than slight angular cheilosis. In view of the persistence of her symptoms over the years, further routine blood investigations were carried out. She was not anaemic (Hb 11.9) and had no macrocytosis (MCV 90.0) but she was found to have a profoundly low level of serum Vitamin B12 (11 ng/l) (laboratory range>190 ng/l). This was checked a month later and still found to be very low at only 29 ng/l. Her serum and red cell folate levels were normal (12 μg/l and 299 μg/l respectively). Further investigations were arranged and the patient was found to have gastric parietal cell antibodies but no intrinsic factor antibodies. Her Schilling test was entirely normal. Monthly injections of hydroxocobalamin were commenced and the patient felt much better. She also found that when she occasionally missed her injections her sore mouth returned. She remained mildly anxious but her neuropsychiatric symptoms were initially much improved.

However, the patient slowly developed memory impairment commencing from around 1998 and her tearfulness recurred. Her memory impairment was characterised by short-term memory problems with a very gradual deterioration. There were no significant behavioural problems but the patient did have difficulty with remembering names and putting names to faces.

On mental examination in March 2000 the patient was pleasant, co-operative, chatty and cheerful. There were no signs of psychomotor agitation or retardation and there were no functional psychotic features. She was not unduly tearful or pessimistic and her talk was rational in form and content. However, there were clear deficits with regard to cognitive function. Although orientated to time, she had demonstrable short-term memory deficits. On the Mini-Mental State Examination (MMSE) she scored 21/30 (16) and it was felt that she had an early dementing illness, perhaps with associated depressive features. She was commenced on antidepressant medication and offered social support.

Although the depressive features slowly resolved over a six month treatment with antidepressants, her cognitive decline continued inexorably. Throughout this time she continued to have regular monthly injections of hydroxocobalamin. One year later, her cognitive skills had declined further. At this time (February 2001) she scored 18/30 on MMSE and had an ADAS-Cog score of 28/70 (17). In view of the persistence of her neuropsychiatric abnormality despite regular hydroxocobalamin, N-acetyl cysteine (600 mg) daily was added to her medication, with informed consent, with the aim of ensuring the presence of a cobalt-sulphur bond in neuronal cobalamin and thereby improve neuronal cobalamin metabolism.

At repeat assessment two weeks later, her husband reported some noticeable improvement in her memory. She was able to remember names and faces that she would otherwise have struggled to recall. She generally felt quite well in herself. Repeat cognitive assessment showed an improvement in her MMSE score to 21/30 and an improvement of eight points on the ADAS-Cog score to 20/70. A seven-point change in the ADAS-Cog score is regarded as clinically significant (18). The main areas of improvement were in scores of orientation, registration, copying skills, word-recall naming and commands. These significant improvements remained at the patient's four-week assessment when the patient gained an additional point on the ADAS-Cog score and demonstrated a dramatic improvement in constructional praxis.

Thus, this study demonstrates that the co-administration of Vitamin $B_{12}$ with compounds that ensure the presence of a cobalt-sulphur bond in neuronal cobalamin (i.e. N-acetyl cysteine) can assist in alleviating the symptoms associated with oxidative stress, such as cognitive decline.

Patient 2:

In 1995 a 70 year old lady presented to her GP with a 1 year history of short term memory loss. She had no significant past medical history. At her initial assessment her cognitive deficits were relatively mild; she scored 27/30 on mini-mental state examination. Nevertheless, she was seen by a psychogeriatrician who felt that, at this time, her cognitive deficits did not warrant a diagnosis of dementia. However, over the following 18 months her memory problems worsened. At a repeat assessment she scored 26/30 on mental state examination, and it was felt that she was probably suffering from "age-associated memory impairment."

Her cognitive function was formally reviewed again 18 months later. Her husband reported that her memory seemed to have deteriorated further, she asked inappropriate questions at times. Her general ability to perform activities of daily living had declined. Her mini-mental state score had declined to 22/30, and it was concluded that she continued to suffer from a slow, age-related cognitive decline. She was commenced on a trial of an acetylcholinesterase inhibitor, but unfortunately had to discontinue this due to troublesome side effects, and there appeared to be no obvious benefit in the first few weeks of treatment anyway.

In 1999 a further formal cognitive assessment was undertaken, and she scored 22/30 on MMSE and 19/70 on an ADAS-Cog assessment. Her most marked areas of deficit were once again related to her short term memory. She had been commenced on folic acid supplements some months previously, but this had resulted in no significant change in her symptoms. She was now found to have a borderline low serum vitamin $B_{12}$ (195 ng/1) and a low plasma glutathione (2.1 μmol/l). She was therefore commenced on monthly injections of hydroxocobalamin. Her husband felt that this resulted in no significant change in her condition. After 6 months later, her cognitive function remained generally unchanged; she scored 21/30 on MMSE. In view of her low glutathione, oral N-acetylcysteine (600 mg) was added to her treatment regime. One month later, her husband reported that she had seemed much more lively in herself, happier, and chattier. Indeed, for the first time in many months her practice nurse noted that she could hold a sensible conversation with her, and that there was a marked improvement in her general behaviour. At formal cognitive assessment her MMSE score had improved dramatically to 25/30—the most striking difference being due to her regaining the ability to remember three objects after several minutes.

This lady suffered from age-associated memory impairment, rather than a dementing illness. Although there was some minor improvement in her symptoms with monthly intramuscular injections of hydroxocobalamin, the addition of oral N-acetylcysteine resulted in a marked improvement in her cognitive scores, particularly with regard to her short-term memory. This example demonstrates the effectiveness of ensuring a cobalt-sulphur bond not only in patients with Alzheimer Disease, but also in cognitive deficits associated with aging in general.

Patient 3:

In 1994 a 77 year old lady presented to her GP with a several month history of increasing confusion and memory loss. An aunt had suffered from early-onset Alzheimer's Disease. On examination she was disorientated to time, but not place Or person. She had a demonstrable impairment of her short term memory. Routine investigations revealed that she was $B_{12}$ deficient (172 ng/l (lab reference range >190 ng/l)), but had normal values of serum folate (10.1 µg/1) and RCF (321 µg/l). In particular, she had no evidence of a macrocytic anaemia (Hb 13.4, MCV 89.2).

She was commenced on monthly injections of hydroxocobalamin (1000 mcg/ml). However, her mental condition continued to deteriorate over the ensuing 2 years, and she began to complain of fatigue and general debilitation. She later developed visual hallucinations, and persecutory ideas secondary to the hallucinations. Cognitive testing at this time (1996) showed that she was poorly orientated in time, although she knew her address, and had a normal working memory. Her anterograde memory was very poor, although her retrograde memory for personal detail was good. Her use of language was generally good, but she had some naming difficulty for low frequency words and her repetition was poor. Her writing was also affected. She showed signs of parietal lobe dysfunction in the form of constructional dyspraxia. Her frontal lobe function was generally good. It was felt that she had a dementing illness of probable Alzheimer-type. She was admitted to a nursing home, but her general condition continued to deteriorate. At a further cognitive review in 1997 she scored only 13/30 on MMSE.

She was commenced on an acetylcholinesterase inhibitor, and her family felt there was some slight improvement in her condition. At repeat assessment she scored 15/30 on MMSE; she remained disorientated in time, but there was no nominal dysphasia and her attention and concentration were reasonable. The drug treatment, together with regular hydroxocobalamin, was therefore continued.

Her physical as well as mental condition continued to deteriorate however, and she developed dysphagia and weight loss in 1998. At this time she scored only 3/10 on an abbreviated mental test. She was admitted to hospital and found to have a grade III oesophagitis. She was treated with a proton-pump inhibitor, and her symptoms of dysphagia slowly resolved.

Nevertheless her general physical and mental condition continued to deteriorate. In June 2001 oral N-acetyl cysteine 600 mg daily was added to her treatment, although she was at this time suffering from a severe degree of dementia. However, her family and the nursing staff noticed and commented upon a significant improvement in her condition in response to this treatment. She became generally more alert and brighter than usual, and seemed to recognise her close family; a formal cognitive assessment was not performed in view of the severity of her dementia and associated physical condition. Her general physical condition deteriorated and she died from a bronchopneumonia several weeks later.

This lady had a dementing illness of probable Alzheimer-type and co-existing vitamin $B_{12}$ deficiency. However it is unlikely that the deficiency was due to malnutrition (she was folate replete) or malabsorption (there was no evidence of a macrocytic anaemia or haematological involvement). It is probable that she had a "functional" vitamin $B_{12}$ deficiency as a consequence of cerebral oxidative stress related to her Alzheimer Disease. An attempt to correct this deficiency with hydroxocobalamin did not prevent her cognitive decline. However, even in the terminal stages of her illness, with its associated physical deterioration, her mental condition improved when N-acetylcysteine was co-administered with hydroxocobalamin to provide a cobalt sulphur bond in the upper axial ligand of neuronal cobalamin.

Patient 4:

In 1994 a 65 year-old male presented to his GP with a three-year history of gradual memory impairment. His wife reported that he would often forget to close doors or would forget to secure his car. There was no history of wandering, or of any features suggestive of a depressive illness. His appetite had been fine, and there was no history of weight loss. He had recently started to have difficulty with washing and dressing himself. He had no significant past medical history, and there was no family history of psychiatric illness or dementia.

Physical examination was unremarkable, and there were no neurological deficits. On mental state examination he was orientated to place and person but not time. He had difficulty copying figures and had a moderate to severe degree of impairment of both recent and remote memory. He lacked insight into his memory loss and denied having any particular worries or problems. He scored 17/30 on Mini-Mental State Examination, and had a CAMDEX score of 54.

Routine blood investigations including full blood count, urea and electrolytes, glucose, liver and thyroid function tests were all within normal limits. His serum vitamin $B_{12}$ and folate levels were also within normal limits at 274 ng/l and 3.9 (ig/l respectively (normal ranges>190 ng/l and >2.2 u.g/l). His red cell folate was also normal at 396 µg/l (normal range>170 µg/l). However, he was found to have a significantly elevated fasting serum homocysteine of 23.7 µmol/l (normal range<13.0 µmol/1). A CT brain scan revealed moderate cerebral atrophy with no other abnormality.

He was reviewed by several psychogeriatricians, and he was diagnosed as having a probable Alzheimer-type dementia. In view of the abnormal homocysteine result he was commenced on monthly injections of hydroxocobalamin (1,000 mg/ml) as well as folic acid supplementation (5 mg daily). However, his cognitive function continued to slowly deteriorate. By 1997 his wife was finding it increasingly difficult to care for him at home. At this time it was felt that he was not a candidate for an acetylcholinesterase inhibitor because of the severity of his dementia. He was admitted to a specialist nursing home for fill time care. Throughout this time he continued with his monthly $B1_2$ injections and oral folate supplements.

A formal re-assessment of his cognitive function was performed in 1999. At this time he scored only 5/30 on Mini-Mental State Examination and 70 on an ADAS-Cog assessment, confining a severe degree of dementia. His serum homocysteine level was now well within normal limits at 5.7 µmol/l, but he was found to have a low plasma level of glutathione at 2.5 µmol/l (normal range 3-5 µmol/l). N-acetylcysteine 600 mg daily was therefore added to his B-vitamin supplementation as an oral glutathione precursor. Although there was no improvement in his cognitive score, he became significantly less agitated, generally more compliant with his nursing care, and his carers noted that his word finding abilities were much improved. In general his behaviour was considerably improved. His wife was particularly impressed by the addition of N-acetylcysteine to his medication; he had even tried to communicate with her for the first time in many years. She was also struck by the fact that he now once again seemed to recognise her when she visited. His clinical improvement was maintained one year later, after his treatment had been changed from N-acetylcysteine to α-lipoic acid 50 mg twice daily as an alternative glutathione precursor.

This patient has probable Alzheimer-type dementia with a co-existing functional vitamin $B_{12}$ deficiency revealed by markedly elevated levels of serum homocysteine. Although treatment with monthly hydroxocobalamin injections and oral folate supplements corrected the levels of serum homocysteine, this did not result in a halting of the dementia process. However, at a late stage of his illness he was found to have low plasma levels of glutathione. Since this is a necessary precursor for the intracellular processing of vitamin $B_{12}$ an attempt was made to increase his glutathione levels by the co-administration of N-acetylcysteine. This resulted in a marked improvement in his general well-being and behavioural symptoms and this clinical improvement continued with the change to an alternative gluthathione precursor, α-lipoic acid. This demonstrates that, even in the advanced stages of a dementing illness, ensuring the provision of a cobalt-sulphur bond in the upper axial ligand of vitamin $B_{12}$ results in clinical improvement.

Patient 5:

A 46-year-old nurse was referred to a specialist Chronic Fatigue Clinic with a history of profound fatigue over many years. She described this as an "incredible fatigue" commencing in her youth.

As part of her investigations, lumbar puncture was performed on two occasions; in April and in September of 1994. Her CSF-homocysteine level was raised on both occasions; 0.42 and 1.00 µmol/L, respectively (ref. <0.25). Serum homocysteine was normal at 13.2 µmol/L, as was serum MMA at 0.10 µmol/L (ref <0.37). Vitamin $B_{12}$ levels in CSF were relatively low at 8.8 (normal values 10-15 pmol/L).

In May 1994 she was commenced on treatment with subcutaneous injections of vitamin $B_{12}$ in the form of methylcobalamin (Methycobal® 0.5 mg/ml) twice weekly. She experienced a clear improvement after only her third injection. She described this as if " . . . my head had been enclosed within a bag, and I was now released." Moreover, a sensation of anaesthesia in the right parts of her jaw and tongue disappeared. After 4 months she reported that her concentration and memory had improved, as had her functions at work, and her sense of general well-being. Gradually her speech improved and she became more fluent and less erroneous (which others had called attention to).

Her vitamin $B_{12}$ injections were withdrawn in September 1994. Two weeks later she was very sensitive to light and sounds, had concentration difficulties and could not complete reading any articles in the daily newspaper. She developed a tingling feeling in her lips, tongue and pharynx, " . . . as when an anaesthesia is fading away". In October of 1994 she was tested by a neuropsychologist (STROOP test) and performed significantly worse than during her treatment period.

She was recommenced on $B_{12}$ injections, and once again felt well until January 1995 when she started clearing another tooth from amalgam At this time she experienced "a paralysing fatigue" and a recurrence of her sensation of facial anaesthesia Although this slowly recovered she still required her vitamin $B_{12}$ injections very frequently (three times weekly). She was genotyped at this time for the thermolabile variant of the methylene tetrahydrofolate reductase gene (MTHFR) and was found to be normal (homozygous for 677C).

She continued to improve slowly over the next few years. By December 1998 although she felt better, she still required sleep of more than 10 hours per night to feel well. In addition to her job, she was also now more actively engaged in the care of her home and two children. She continued to attend the Chronic Fatigue clinic. In April 2001 oral N-Acetylcysteine 400 mg daily was added to her vitamin $B_{12}$ regime. After only a month she felt "more lively and with less headaches." She felt very positive about this addition to her treatment and was adamant that she continue it, in spite of some gastroenteric side effects. She continued to improve, and after three months did not require as much sleep as previously. Most significantly she was now able to reduce the frequency of her vitamin $B_{12}$ injections to once weekly. Also, she now reported that her headaches had almost completely disappeared.

This patient had clinical features of a Chronic Fatigue Syndrome, and also displayed an error of vitamin $B_{12}$ metabolism in the central nervous system. This was revealed by increased levels of homocysteine in her cerebrospinal fluid suggesting a functional vitamin $B_{12}$ deficiency. Her clinical condition stabilised very slowly but dramatically over the years. She is probably hypersensitive to metals, including nickel, and clearance of the tooth amalgam might have contributed to the improvement However, she clearly improved in relation to the commencement of her methylcobalamin injections; its effects were confirmed by the marked deterioration in relation to the withdrawal of these injections in 1994. The addition of the glutathione precursor N-acetylcysteine to her vitamin $B_{12}$ therapy resulted in a marked further improvement in her clinical condition, and she was also able to significantly reduce the frequency of these injections.

Patient 6:

A 54-year-old female physician had first become acutely ill when she was 39. The symptoms and signs suggested a brain stem affectation, and she was diagnosed as suffering from multiple sclerosis. She exhibited "slow cerebration" and felt fatigued and hypersomnic. Although she improved slowly over the next 3-4 years, she also developed some new symptoms including a feeling of 'heaviness' in her legs, a slightly impaired gait, difficulty in raising herself from a sitting to a standing position, blurred vision in one eye, proprioceptive difficulties, and impaired orientation in time and space.

At the age of 44 her urinary homocysteine was assayed. This was elevated and she was therefore commenced on regular injections of vitamin $B_{12}$. She soon noticed a very apparent improvement in her symptoms; all her visual and proprioceptive complaints improved, as did her orientation.

However, she still retained some signs of a 'brain lesion syndrome'; one neurologist best described this as an asthenoemotional syndrome, including discrete signs of right-sided facial paralysis, dysarthria and an auditive aphasia The auditive aphasia was compensated for by head-phones and an electronic apparatus which synchronizes sound better. Although slowly improving, her persistent chronic fatigue and stress intolerance have made it impossible for her to return to work as a physician.

At the age of 54, her medication comprised 1 mg of oral cobalamin and 5 mg of folic acid daily. NAC was then added to this regime. After 4 months she reported that she had only been able to take 100 mg daily because of gastro intestinal side effects. Nevertheless, she felt 'definitely improved'. She found that she had fewer headaches. Her concentration had improved which now enabled her to read and understand even complex matters. Her fatigue was less severe, and she was able to sleep for longer periods at night.

This physician had a presumed diagnosis of multiple sclerosis. She was found to have evidence of a functional $B_{12}$ deficiency, revealed by elevated urinary homocysteine levels. Although her symptoms improved with vitamin $B_{12}$ supplementation, the co-administration of N-acetylcysteine, to provide a cobalt-sulphur bond in the upper axial ligand of cobalamin, resulted in a further marked improvement in her symptoms.

Patient 7:

in 1996 an 81-year old gentleman was brought to the attention of his GP with regard to deterioration in his short-term memory over the previous five years. He had no significant relevant past medical history. There was a family history of Parkinsonism and cerebrovascular accident in two of his siblings.

On examination, he had a slightly irregular pulse, borderline hypertension (150/90) and was noted to have cold extremities, but no other obvious abnormalities. He was unable to remember three words after a few minutes. Routine investigations revealed no abnormalities; in particular he was not anaemic (Hb 14.7), had a normal MCV, normal levels of total serum $B_{12}$ (324 ng/l) and folate (13.3 µg/l), and normal thyroid function tests.

It was felt that he was suffering from a senile dementia. His condition continued to deteriorate gradually, but then became dramatically worse in a matter of a few weeks in 1997. At this time, he had frequent falls, and had become increasingly confused. It was noted that he tended to fall towards the right, and he had right-sided weakness, and an equivocal right plantar reflex. It was felt that he had sustained a probable TIA, and he was admitted to hospital. CT scan showed a lacunar infarct. He also developed a chest infection. This was treated with antibiotics, and his confusion and mobility improved slightly. He was commended on aspirin and discharged home.

However, he continued to deteriorate over the ensuing months, became verbally aggressive at times, exhibited repetitive speech, and became increasingly agitated. On cognitive assessment in 1998 he was disorientated to year, unable to name the prime minister, or US president, could not recall the examiners name after a few minutes, and had difficulty with visuo-spatial awareness, manifested by the inability to draw numbers correctly on a clock-face, and inability to copy a 3-dimensional cube figure. He had no depressive features, no delusional thought, no communication problems, or sleep disturbance. It was noted that he had an unsteady gait, and was beginning to need assistance with most activities of daily living. However, there was some improvement in his condition over the ensuing few weeks, and he was therefore discharged from the care of the Psychogeriatric assessment services at this time.

In 1999, he developed a disturbed sleep pattern and increasing cognitive deficits. His agitation worsened, but was controlled with thioridazine. He sustained a further few falls, and required hospital admission for these by the end of the year. Overall, his general condition had worsened and his wife now found it difficult to cope and care for him at home. He now had word finding difficulties and frequently confabulated, had deterioration of his self-care, frequently wandered, was unsteady on his feet, lacked insight, and had developed an irritable, resentful and suspicious mood, very much unlike his pleasant pre-morbid character.

He was admitted for full-time care, initially in a residential home, but was shortly transferred to a nursing home, as they were unable to cope with his increasingly demanding behaviour.

In 2001 he was found to have raised plasma homocysteine level of 19.8 µmol/l (normal level<16 µmol/l), a lower $B_{12}$ and folate than previously (297 ng/l and 4.7 µg/l respectively), although he still had a normal red cell folate of 204 µg/l, and no evidence of macrocytic anaemia (Hb13.4, MCV 91). He therefore had evidence of a functional vitamin $B_{12}$ deficiency, and was commenced on weekly hydroxocobalamin injections together with an oral folate supplement. However, there was no significant improvement in his cognitive function. At this time, he scored 68 on an ADAS-Cog assessment demonstrating a significant degree of dementia. 600 mg NAC daily was added to his treatment regime to indirectly provide a cobalt-sulphur bond in the upper axial ligand of cobalamin. After one mouth's treatment, he had gained 6 points on his ADAS-Cog score. The staff at the home commented that he was less agitated, and more contented. In particular his wife felt that he was a lot better in himself, more settled, and generally more alert.

The "stepwise" deteriorating course in this gentleman's condition, patchy distribution of deficits, borderline hypertension, cold extremities, family history of cerebrovascular accident, focal neurological signs and symptoms, and sudden deterioration in symptomatology in association with a lacunar infarct on CT scan, strongly support a diagnosis of vascular dementia in this gentleman. Furthermore, he had biochemical evidence for a functional vitamin $B_{12}$ deficiency, in the absence of anaemia. This example demonstrates that in patients with vascular dementia, there is a significant clinical improvement with the co-administration of hydroxocobalamin and N-acetylcysteine to indirectly generate a cobalt-sulphur bond in the upper axial ligand of cobalamin.

EXAMPLE 3

Plasma homocysteine levels are elevated in Alzheimer Disease, but little is known regarding the levels of other aminothiols in the disease. Evaluating the levels of these associated metabolites will assist in determining the biochemical locus for the elevated homocysteine. Therefore, total plasma homocysteine, cysteine, glutathione and cysteinylglycine levels were determined in patients and controls and their relationship with cognitive scores was investigated.

Fifty patients with features compatible with DSM-IV criteria for primary degenerative dementia of Alzheimer-type, and fifty-seven cognitively intact age-sex matched control subjects had their MMSE and ADAS-Cog scores determined. Aminothiols were assayed with the Drew Scientific DS30 Hcy Analyser. Subjects using homocysteine disruptive medication including vitamin $B_{12}$, folic acid and hormone replacement therapy were excluded from data analysis. MMSE and ADAS-Cog scores were recorded for cases and controls (16, 17). The latter instrument addresses several cognitive domains and is well validated. It is sensitive to cognitive changes over time and so provides a useful baseline for future studies.

Prior education of the subjects was also determined ("none, primary, intermediate, secondary and further") since this relates to cognitive decline in normal aging (19). Smoking ("current, ex, and never") and hypertensive status were also documented, these being associated with modest elevation of homocysteine (20). For the purpose of statistical analysis, prior education and smoking were treated as ordinal variables and hypertensive status as a categorical variable. Height and weight were measured at assessment to calculate body mass index (BMI). Ethical approval was granted, and informed consent obtained.

Non-fasting blood samples were taken for full blood count, red cell folate (RCF), creatinine, $B_{12}$, folate, and aminothiol assays. Separation and freezing were performed within one hour of venepuncture until aminothiol analysis (21).

An automated cell counter was used to measure haemoglobin (Hb) concentration, and mean corpuscular volume (MCV) (Coulter Gen-S, Beckman Coulter, High Wycombe, Bucks, UK). An automated biochemistry analyser was used to analyse creatinine (Synchron LX-20 analyser, Beckman Coulter, High Wycombe, Bucks, UK) and an automated chemiluminescence analyser was used to measure folate, vitamin $B_{12}$ and RCF (ACS:180 SE, Bayer plc, Newbury, Berks UK) using the manufacturers' recommended protocols. Aminothiols were assayed with an automated HPLC system (DS30 Hcy Analyser, Drew Scientific Group plc, Barrow in Furness, Cumbria, UK) For each aminothiol, all forms including protein bound, non-protein bound, free forms both oxidized (dimer and mixed disulphides) and reduced were measured. Values presented always refer to "total" plasma levels.

Comparisons between groups (Wilcoxon-Mann-Whitney test), 95% confidence intervals for differences between medians (Hodges-Lehmann estimates) and measures of association (Spearman rank-order correlation coefficient) were performed using exact, non-parametric methods (StatXact 4 for Windows, Cytel Software Corporation, Cambridge, Mass.). Conventional techniques were used for regression analysis and generalised linear modelling (Statistica for Windows v5.5, StatSoft, Inc., Tulsa, Okla.). Ridge regression, an extension to conventional regression analysis, was used to correct for possible correlations among the independent variables. For the purpose of generalised linear modelling, continuous variables were specified as the dependent variables, a linear link function was used and mixtures of categorical, ordinal and continuous variables specified as the independent variables. The significance of the model parameters were assessed using a $\chi^2$ test. Median results are presented with interquartile ranges and simple regression coefficients are presented with their 95% confidence intervals (95% CI).

Results:

There were 50 AD patients (17 male and 33 female) and 57 controls (23 male and 34 female). The median age of both groups was 79 years (75-83 for AD and 72-85 for controls). AD patients had a median duration of disease of 24 (13-36) months and a median age of onset of 77 (74-82) years.

There was no difference in BMI, prior education or smoking status between patients and controls. Patients had lower median systolic blood pressure than controls (patients: 130 (120-140) mmHg, controls: 145 (130-160) mmHg, 95% CI for difference: 0 to 20, p=0.01) and lower median diastolic blood pressure (patients: 80 (70-82) mmHg, controls: 85 (79-95) mm g, 95% CI for difference: 5 to 10, p=0.0005).

Plasma samples were stored for a median of 12 months prior to aminothiol assay (range 1 to 23 months). Regression analysis was used to assess the effect of storage time on these assays. Within the aggregated data (patients plus controls), storage time had no effect upon homocysteine or glutathione levels. There was a small decrease in cysteine and cysteinylglycine levels with storage time: cysteine=142.3−2.33×storage time in months (p=0.0002, 95% CI: −3.52 to −1.14), cysteinylglycine=20.9−0.26×storage time in months (p=0.007, 95% CI: −0.43 to −0.09). The addition of diagnosis as an additional categorical independent variable demonstrated no difference in the effect of storage between patients and controls.

AD patients were found to have significantly decreased folate, and significantly increased plasma homocysteine and cysteine. Hb, platelets, MCV, creatinine, $B_{12}$, RCF, cysteinylglycine and glutathione did not differ between groups, as shown in Table 3 below.

Figure 5:
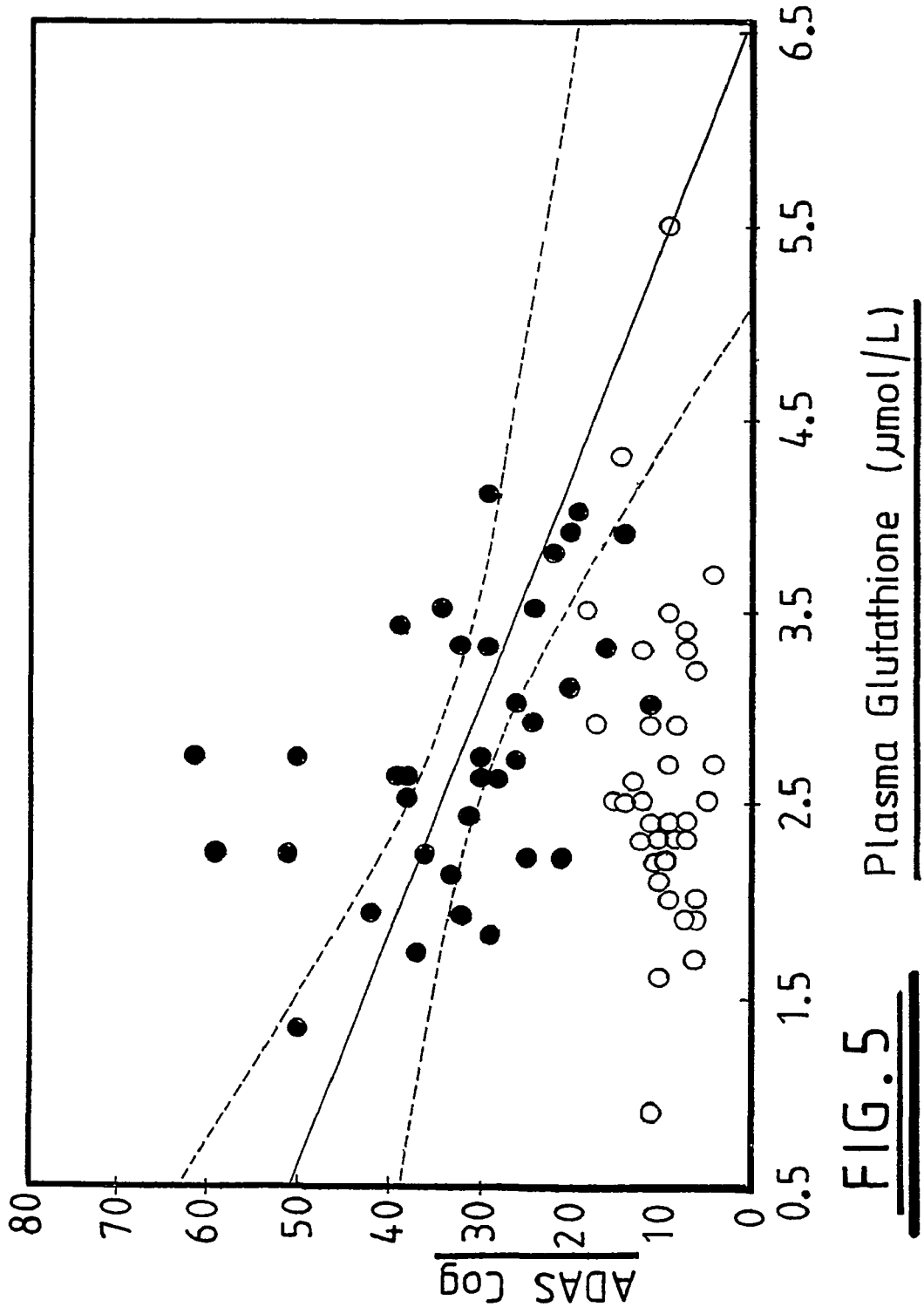
FIG. 5 is a scatter diagram showing the relationship between ADAS-Cog score and plasma glutathione in patients with DSM-IV criteria for primary degeneration dementia of Alzheimer type (filled circles) and controls (open circles).

Among the patients, a decrease in MMSE score was associated with a decrease in plasma glutathione: MMSE=8.27+3.56×glutathione (p=0.002, 95% CI: 0.29 to 6.82). Similarly, an increase in ADAS-Cog score was associated with a decrease in plasma glutathione: ADAS-Cog=54.9−8.39×glutathione (p=0.002, 95% CI: −13.6 to −3.22), see FIG. 5. To protect against the possibility that these relationships were artefacts caused by a correlation between plasma glutathione and homocysteine, itself known to affect cognitive function (1), (3), a ridge regression analysis was performed with plasma homocysteine, cysteine and cysteinylglycine as additional independent variables. This analysis confirmed that plasma glutathione was the only aminothiol to be an independent statistically significant predictor of MMSE and ADAS-Cog scores.

Among the controls, there was no relationship between MMSE and glutathione, homocysteine, cysteine and cysteinylglycine. There was an increase in ADAS-Cog with decreasing plasma glutathione: ADAS-Cog=29.6−0.61×glutathione (p=0.04, 95% CI: −1.21 to −0.002), but this relationship was abolished with the addition of homocysteine, cysteine and cysteinylglycine in a ridge regression model.

Other possible confounding factors that might influence the relationship between plasma glutathione and cognitive score are age, smoking status, presence of hypertension, and years of education. A generalised linear modelling technique was used to assess the effect of these factors plus plasma glutathione on ADAS-Cog and MMSE scores. The results confirmed that glutathione is an independent predictor of cognitive performance in this study, see Table 4 below.

TABLE 4

| Scoring system | Independent variable | Log-likelihood | $\chi^2$ (1 d.f.) | p-value |
| --- | --- | --- | --- | --- |
| ADAS-Cog | Age | −72.33 | 0.35 | 0.55 |
| | Education | −76.55 | 8.78 | 0.003 |
| | Smoking | −72.42 | 0.52 | 0.47 |
| | Glutathione | −75.15 | 5.98 | 0.014 |
| | Hypertension | −76.83 | 9.34 | 0.002 |
| MMSE | Age | −56.98 | 0.0001 | 0.99 |
| | Education | −58.26 | 2.56 | 0.11 |
| | Smoking | −57.33 | 0.69 | 0.40 |
| | Glutathione | −60.57 | 7.18 | 0.007 |
| | Hypertension | −58.59 | 3.22 | 0.07 |

Thus, glutathione was found to be a highly significant and independent predictor of cognitive scores in patients

TABLE 3

| | Controls | Patients | p-value (95% CI of difference between medians) |
| --- | --- | --- | --- |
| BMI | 24.1 (22.1-28.4) | 24.6 (22.5-27.4) | |
| MMSE | 28 (27-29) | 18 (14-21) | p < 0.0001 (8-12) |
| ADAS-Cog | 9 (7-12) | 32 (24-39) | p < 0.0001 (19-26) |
| Hb, g/dl | 13.4 (12.5-14.4) | 12.9 (12.0-14.2) | |
| Platelets, ×10$^9$/l | 218 (184-277) | 216 (182-273) | |
| MCV, fl | 90.4 (87.8-94.0) | 90.4 (88.4-93.6) | |
| Creatinine, μmol/l | 84 (72-102) | 87 (72-115) | |
| $B_{12}$, ng/l | 324 (276-445) | 334 (268-421) | |
| Folate, μg/l | 10.5 (8.1-14.5) | 9.0 (6.3-11.6) | p = 0.018 (0.4-3.8) |
| RCF, μg/l | 330 (272-425) | 282 (243-399) | |
| Homocysteine, (μmol/l) | 9.6 (8.2-12.5) | 12.6 (9.6-15.8) | p = 0.0006 (1.2-4.3) |
| Cysteine, (μmol/l) | 107.2 (94.7-129.4) | 120.1 (102.0-142.4) | p = 0.007 (3.6-23.7) |
| Cysteinylglycine, (μmol/l) | 17.7 (15.5-20.3) | 17.5 (15.4-21.1) | |
| Glutathione, (μmol/l) | 2.5 (2.2-2.9) | 2.7 (2.2-3.3) | |

(p=0.002); lower plasma levels were associated with more severe cognitive impairment. Plasma homocysteine and cysteine are elevated in Alzheimer Disease implying intact and increased transsulphuration but aberrant re-methylation of homocysteine in patients. These findings reflect the differential effects of oxidative stress on key enzymes of sulphur amino acid metabolism.

Glutathionylcobalamin and related thiolatocobalamins may also be used to prevent a functional Vitamin $B_{12}$ deficiency in all diseases and disorders associated with low intracellular glutathione, including aging. It is to be appreciated that such patients would, eventually, develop a functional $B_{12}$ deficiency anyway but in the early stages of disease might not have clear metabolic evidence of such deficiency.

Reduced glutatione levels in mammalian cells are associated with a wide range of pathophysiologic states, including hepatic dysfunction, malignancies, HIV infection, pulmonary disease, Parkinson's disease, related immunologic illnesses and physiological conditions. The following list is for example purposes only and is not exhaustive:

Acetaminophen poisoning, ADD, Addision's Disease, aging, AIDS, Alopecia Areata, ALS, Alzheimers' Disease, anemia (hemolytic), Ankylosing Spondylitis, Arteriosclerosis (hardening of the arteries), arthritis (rheumatoid), asthma, autism, autoimmune disease, Behcet's Disease, burns, cachexia, cancer, candida infection, cardiomyopathy (idiopathic), Chronic Fatigue Syndrome, colitis, coronary artery disease, cystic fibrosis, diabetes, Crohn's disease, Down's syndrome, eczema, emphysema, Epstein Barr Viral (EBV) syndrome, fibromyalgia, free radical overload, Goodpasture Syndrome, Graves' Disease, hepatic dysfunction (liver disease), hepatitis B, hepatitis C, hypercholesterolemia (high blood cholesterol), herpes, infections (viral, bacterial and fungal), inflammatory bowel disease (IBD), lupus, macular degeneration (senile and diabetic macular degeneration), malnutrition, Meniere's disease, multiple sclerosis, Myasthenia Gravis, neurodegenerative diseases, nutritional disorders, Parlinson's disease, Pemphigus Vulgaris, Primary Biliary Cirrhosis, progeria, psoriasis, Rheumatic Fever, Sarcoidosis, scleroderma, shingles, stroke, toxic poisoning, vasculitis, vitiligo, and Wegener's Granulomatosis.

REFERENCES CITED

1. McCaddon et al., [1998] Total Serum Homocysteine in Senile Dementia of Alzheimer Type. *Int. J. Psych.* 13 235-239.
2. Clarke et al., [1998] Folate, Vitamin $B_{12}$ and Serum Total Homocysteine levels in confirmed Alzheimers Disease. *Arch. Neurol.* 55 1449-55.
3. Lehmann et al., [1999] Identification of cognitive impairment in the elderly; Homocysteine is an early marker. Dement. *Genatr. Cogn. Disord.* 10.12-20.
4. Seshadri et al., [2002]. Plasma homocysteine as a risk factor for dementia and Alzheimer's Disease. *N. Engl. J. Med.* 346(7), 476-483.
5. McCaddon et al; [2001] Homocysteine and cognitive decline in healthy elderly. *Dement. Geriatr, Cogn. Disord* 12 309-313.
6. Kristensen et al., [1993] Serum cobalamin and methylmalonic acid in Alzheimer dementia *Acta. Neurol. Scand.* 87, 475-481.
7. Lindenbaum et al., [1998] Neuropsychiatric disorders caused by cobalamin deficiency in the absence of anaemia or macrocytosis. *N. Engl. J. Med.* 318, 1720-1728.
8. Selley M L et al [2002] The effect of increased concentrations of homocysteine on the concentration of (E)-4-hydroxy-2-nonenal in the plasma and cerebrospinal fluid of patients with Alzheimer's disease. *Neurobiol Aging May-June;* 23(3), 383-8.
9. Chen et al., [1999]. Homocysteine metabolism in cardiovascular cells and tissues: implications for hyperhomocysteinemia and cardiovascular disease. Adv. *Enzyme Regul.* 39, 93-109.
10. Mosharov, E. et al. [2000]. The quantitatively important relationship between homocysteine metabolism and glutathione synthesis by the transsulfuration pathway and its regulation by redox changes. *Biochemistry* 39, 13005-13011.
11. Christen, Y. [2000]. Oxidative stress and Alzheimers disease. *Am. J. Clin. Nutr.* 71 (suppl), 621S-629S.
12. Berr et al., [2000]. Cognitive decline associated with systemic oxidative stress: The EVA Study. JAGS 48, 1285-1291.
13. Kondo et al. [1981] "Nitrous oxide has multiple deleterious effects on cobalamin metabolism and causes decreases in activities of both mammalian cobalamin dependent enzymes in rats." *J. Clin. Invest.* 67, 1270-1283.
14. McCaddon et al. [2001] "Analogues, ageing and aberrant assimilation of vitamin B12 in Alzheimer's Disease." *Dement. Geriatr. Cogn. Disord.* 12(2) 133-137.
15. Pezacka [1993]. Identification and characterization of two enzymes involved in the intracellular metabolism of cobalamin. Biochim. Biophys. Acta. 1157, 167-177.
16. Folstein M et al., [1975] Mini-Mental State: A practical method for grading the cognitive state of patients for the clinician. *J. Psychiatr. Res* 12, 189-98.
17. Rosen W G et al., [1984] A new rating scale for Alzheimers Disease. Am J Psychaitr. 141, 1356-64
18. Warner J et al., [1999] Alzheimers Disease. *Clinical Evidence* 2, 341-346.
19. Jacqmin-Gadda et al., [1997]. A 5 Year longitudinal study of the Mini-Mental State Examination in Normal Aging. *Am. J. Epidemiol.* 145(6): 498-506.
20. Nygard et al., [1995]. Total Plasma Homocysteine and Cardiovascular Risk Profile. The Hordaland Homocysteine Study. *JAMA.* 274 (19), 1526-33.
21. Andersson et al., [1992]. Homocysteine Export from Erythrocytes and its implication for plasma sampling. *Clin. Chem.* 38(7), 1311-5.

The invention claimed is:

1. A method for treating an individual having a disease selected from the group consisting of Alzheimer's disease, age-related cognitive decline, mild cognitive impairment, senile dementia, chronic fatigue syndrome, multiple sclerosis, vascular dementia, depression, and vascular disease; wherein the disease has symptoms associated with a functional Vitamin $B_{12}$ deficiency; said method comprising administering to the individual a therapeutically effective amount of a composition or compositions that comprise:
   (i) a first component selected from the group consisting of Vitamin $B_{12}$ (cyanocobalamin), hydroxycobalamin, and methylcobalamin; and (ii) a second component which is N-acetyl cysteine; wherein the first and second components may be administered concurrently or separately;
   Wherein: the individual's intracellular processing of cobalamin increases after administering the composition or compositions, and the symptoms associated with the functional Vitamin $B_{12}$ deficiency improve.

2. A method as in claim 1, wherein the disease is age-related cognitive decline.

3. A method as in claim 1, wherein the disease is senile dementia.

4. A method as in claim 1, wherein the disease is Alzheimer's disease.

5. A method as in claim 1, wherein the disease is vascular dementia.

6. A method as in claim 1, wherein the disease is mild cognitive impairment.

7. A method as in claim 1, wherein the disease is chronic fatigue syndrome.

8. A method as in claim 1, wherein the disease is multiple sclerosis.

9. A method as in claim 1, wherein the disease is depression.

10. A method as in claim 1, wherein the disease is vascular disease.

* * * * *